US012611508B2

(12) United States Patent
Judson

(10) Patent No.: US 12,611,508 B2
(45) Date of Patent: Apr. 28, 2026

(54) MEDICATION DELIVERY DEVICE WITH NEEDLE CARRIER

(71) Applicant: Eli Lilly and Company, Indianapolis, IN (US)

(72) Inventor: Jared Alden Judson, Medford, MA (US)

(73) Assignee: Eli Lilly and Company, Indianapolis, IN (US)

( * ) Notice: Subject to any disclaimer, the term of this patent is extended or adjusted under 35 U.S.C. 154(b) by 1085 days.

(21) Appl. No.: 17/641,849

(22) PCT Filed: Sep. 4, 2020

(86) PCT No.: PCT/US2020/049412
§ 371 (c)(1),
(2) Date: Mar. 10, 2022

(87) PCT Pub. No.: WO2021/050380
PCT Pub. Date: Mar. 18, 2021

(65) Prior Publication Data
US 2024/0042133 A1 Feb. 8, 2024

Related U.S. Application Data

(60) Provisional application No. 62/898,810, filed on Sep. 11, 2019.

(51) Int. Cl.
*A61M 5/28* (2006.01)
*A61M 5/20* (2006.01)
(Continued)

(52) U.S. Cl.
CPC .............. *A61M 5/281* (2013.01); *A61M 5/20* (2013.01); *A61M 5/2422* (2013.01);
(Continued)

(58) Field of Classification Search
CPC ...... A61M 5/281; A61M 5/20; A61M 5/2422; A61M 5/285; A61M 5/31; A61M 5/3137;
(Continued)

(56) References Cited

U.S. PATENT DOCUMENTS 5,762,634 A 6/1998 Davis
5,779,683 A 7/1998 Meyer
(Continued)

FOREIGN PATENT DOCUMENTS

WO 2009091709 7/2009
WO 2010048753 A1 5/2010
(Continued)

OTHER PUBLICATIONS

"BD AutoShield Duo™ pen needle," BD, Retrieved Feb. 12, 2019, from https://www.bd.com/en-ca/offerings/capabilities/diabetes-care/pen-needles/bd-autoshield-duo-pen-needle.
(Continued)

*Primary Examiner* — Tasnim Mehjabin Ahmed
(74) *Attorney, Agent, or Firm* — M. Daniel Spillman

(57) ABSTRACT

Drug delivery devices are provided having a needle assembly portion and a drug device portion, where the needle assembly portion is removably coupleable to the drug device portion. In some embodiments, the needle of the needle assembly may be moveable between a retracted position and an extended position for piercing into a subjects skin.

27 Claims, 18 Drawing Sheets

(51) Int. Cl.

| | |
|---|---|
| *A61M 5/24* | (2006.01) |
| *A61M 5/31* | (2006.01) |
| *A61M 5/315* | (2006.01) |
| *A61M 5/32* | (2006.01) |
| *A61M 5/34* | (2006.01) |
| *A61M 5/50* | (2006.01) |

(52) U.S. Cl.
CPC .............. *A61M 5/285* (2013.01); *A61M 5/31* (2013.01); *A61M 5/3137* (2013.01); *A61M 5/31511* (2013.01); *A61M 5/3202* (2013.01); *A61M 5/3221* (2013.01); *A61M 5/3234* (2013.01); *A61M 5/3287* (2013.01); *A61M 5/3293* (2013.01); *A61M 5/34* (2013.01); *A61M 5/50* (2013.01); *A61M 2005/2006* (2013.01); *A61M 2202/0007* (2013.01); *A61M 2205/10* (2013.01); *A61M 2205/123* (2013.01); *A61M 2205/19* (2013.01); *A61M 2205/273* (2013.01)

(58) Field of Classification Search
CPC ............ A61M 5/31511; A61M 5/3202; A61M 5/3221; A61M 5/3234; A61M 5/3287; A61M 5/3293; A61M 5/34; A61M 5/50
See application file for complete search history.

(56) References Cited

U.S. PATENT DOCUMENTS

| | | | |
|---|---|---|---|
| 6,342,045 | B1 | 1/2002 | Somers |
| 7,056,306 | B1 | 6/2006 | Halseth et al. |
| 2001/0053886 | A1 | 12/2001 | Caizza |
| 2002/0007103 | A1 | 1/2002 | Fontayne et al. |
| 2003/0032927 | A1 | 2/2003 | Halseth et al. |
| 2003/0045838 | A1 | 3/2003 | Woodard, Jr. et al. |
| 2004/0236284 | A1 | 11/2004 | Hoste et al. |
| 2005/0027255 | A1 | 2/2005 | Lavi et al. |
| 2005/0124940 | A1 | 6/2005 | Martin et al. |
| 2006/0287630 | A1 | 12/2006 | Hommann |
| 2007/0088268 | A1 | 4/2007 | Edwards |
| 2007/0106225 | A1 | 5/2007 | Millerd |
| 2007/0255221 | A1 | 11/2007 | Nakajima |
| 2008/0039795 | A1 | 2/2008 | Slate et al. |
| 2008/0177235 | A1 | 7/2008 | DiBiasi |
| 2008/0215001 | A1 | 9/2008 | Cowe |
| 2008/0269687 | A1* | 10/2008 | Chong ................ A61M 5/1413 604/180 |
| 2011/0022001 | A1 | 1/2011 | Wei |
| 2011/0023644 | A1 | 2/2011 | Ramadoss et al. |
| 2011/0071492 | A1 | 3/2011 | Horvath et al. |
| 2011/0106008 | A1 | 5/2011 | Kronestedt |
| 2011/0106016 | A1* | 5/2011 | Wei ..................... A61M 5/2466 604/201 |
| 2011/0118667 | A1 | 5/2011 | Zaiken et al. |
| 2011/0238009 | A1* | 9/2011 | Meron ................ A61M 5/3294 604/82 |
| 2011/0270188 | A1 | 11/2011 | Caffey et al. |

| | | | |
|---|---|---|---|
| 2012/0022499 | A1 | 1/2012 | Anderson et al. |
| 2012/0041373 | A1 | 2/2012 | Bruehwiler et al. |
| 2012/0130318 | A1 | 5/2012 | Young |
| 2012/0143144 | A1 | 6/2012 | Young |
| 2012/0265136 | A1 | 10/2012 | Lawlis et al. |
| 2013/0006179 | A1 | 1/2013 | Iwase et al. |
| 2013/0018313 | A1 | 1/2013 | Kramer et al. |
| 2013/0060196 | A1 | 3/2013 | O'Connor et al. |
| 2013/0060233 | A1 | 3/2013 | O'Connor et al. |
| 2013/0123710 | A1 | 5/2013 | Ekman et al. |
| 2013/0218128 | A1 | 8/2013 | Cowe |
| 2013/0253472 | A1 | 9/2013 | Cabiri |
| 2013/0289490 | A1 | 10/2013 | Kemp et al. |
| 2014/0207106 | A1 | 7/2014 | Bechmann et al. |
| 2014/0213975 | A1 | 7/2014 | Clemente et al. |
| 2014/0221936 | A1 | 8/2014 | Edhouse et al. |
| 2014/0343507 | A1 | 11/2014 | Karlsson et al. |
| 2015/0051553 | A1 | 2/2015 | Björk et al. |
| 2015/0100029 | A1 | 4/2015 | Cowe et al. |
| 2015/0174335 | A1 | 6/2015 | Roervig et al. |
| 2015/0202366 | A1 | 7/2015 | Henderson et al. |
| 2015/0283323 | A1 | 10/2015 | Young et al. |
| 2016/0045680 | A1 | 2/2016 | Morris |
| 2016/0175524 | A1 | 6/2016 | Henderson et al. |
| 2016/0271319 | A1 | 9/2016 | Bengtsson et al. |
| 2017/0173304 | A1 | 6/2017 | Teoh |
| 2017/0259011 | A1 | 9/2017 | Nielsen |
| 2018/0021508 | A1 | 1/2018 | Destefano et al. |
| 2018/0064883 | A1 | 3/2018 | Calvert |
| 2018/0185582 | A1 | 7/2018 | Mikkelsen |
| 2018/0339098 | A1 | 11/2018 | Larsen et al. |
| 2018/0353693 | A1* | 12/2018 | Wendland ........... A61M 5/3202 |
| 2018/0353708 | A1 | 12/2018 | Schader et al. |
| 2018/0361069 | A1 | 12/2018 | Schader et al. |
| 2019/0117880 | A1 | 4/2019 | Hirschel et al. |
| 2019/0328968 | A1 | 10/2019 | Giambattista |
| 2020/0297580 | A1 | 9/2020 | Liscio |
| 2020/0405950 | A1 | 12/2020 | Burren et al. |
| 2021/0128817 | A1 | 5/2021 | Bengtsson et al. |

FOREIGN PATENT DOCUMENTS

| | | |
|---|---|---|
| WO | 2017016986 A1 | 2/2017 |
| WO | 2018204779 | 11/2018 |
| WO | 2019106164 | 6/2019 |
| WO | 2019112886 A1 | 6/2019 |
| WO | 2019122946 | 6/2019 |
| WO | 2021050380 A1 | 3/2021 |

OTHER PUBLICATIONS

Patent Cooperation Treaty International Search Report pertaining to International Application No. PCT/US2020/049412; International Filing Date: Sep. 4, 2020; Date of Mailing: Nov. 20, 2020.
Patent Cooperation Treaty Written Opinion of the International Searching Authority pertaining to International Application No. PCT/US2020/049412; International Filing Date: Sep. 4, 2020; Date of Mailing: Nov. 20, 2020.

* cited by examiner

MEDICATION DELIVERY DEVICE WITH NEEDLE CARRIER

BACKGROUND

Patients suffering from a number of different diseases frequently must inject themselves with medication. To allow a person to conveniently and accurately self-administer medicine, a variety of devices broadly known as injector pens or injection pens have been developed. Generally, these pens are equipped with a medicament container such as a cartridge including a piston and containing a multi-dose quantity of liquid medication. A drive member, extending from within a base of the injector pen and operably connected with mechanisms of the pen that control drive member motion, is movable forward to advance the piston in the cartridge in such a manner to dispense the contained medication from an outlet at the opposite cartridge end, typically through a needle that penetrates a stopper at that opposite end. In disposable or prefilled pens, after a pen has been utilized to exhaust the supply of medication within the cartridge, a user, who then begins using a new replacement pen, discards the entire pen. In reusable pens, after a pen has been utilized to exhaust the supply of medication within the cartridge, the pen is disassembled to allow replacement of the spent cartridge with a fresh cartridge, and then the pen is reassembled for its subsequent use.

The inventors have appreciated that, with some drug delivery devices, a user may be required to attach and/or detach a needle from the drug delivery device prior to and/or after use. The inventors have recognized a need for an arrangement that facilitates attachment and detachment of a needle assembly from the drug delivery device.

SUMMARY

According to one aspect, a drug delivery device is provided. The drug delivery device may include, in some embodiments, a needle assembly including a needle carrier, a needle hub moveable within the needle carrier, and a needle coupled to the needle hub. The drug delivery device may include a drug device having a needle drive, and the needle carrier is coupleable to the drug device to position the proximal end of the needle inserted through a septum in fluid communication within a container of the drug delivery device. The drug delivery device may include an actuator configured to activate the needle drive to move the needle hub distally relative to the septum from a retracted needle hub position to an extended needle hub position and to move the needle distally from a retracted needle position to an extended needle position.

According to another aspect, a method is provided. The method may include, in some embodiments, steps of providing a drug device having a drive gear and providing a needle assembly including a needle carrier, a needle hub movable relative to the needle carrier, a needle coupled to the needle hub, and a cam configured to move the needle hub. The method may also include mounting the needle assembly to the drug device to couple the cam to the drive gear, actuating the drive gear to rotate the cam to drive the needle hub distally to move the needle to an extended position, and actuating the drive gear to rotate the cam to drive the needle hub proximally to move the needle to a retracted position.

According to another aspect, a needle assembly for coupling to a drug device and a container is provided. The container includes a septum and includes a fluid. The needle assembly includes a needle carrier coupleable to the drug device to pierce the septum. A cam is within the needle carrier and the cam has a driven gear. A needle hub is coupled to the cam and is movable relative to the needle carrier. A needle is coupled to the needle hub. In response to rotating the driven gear of the cam, the cam is configured to drive the needle hub to at least one of to move the needle in an extension direction and to drive the needle hub to move the needle in a retraction direction.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Additional embodiments of the disclosure, as well as features and advantages thereof, will become more apparent by reference to the description herein taken in conjunction with the accompanying drawings. The components in the figures are not necessarily to scale. Moreover, in the figures, like-referenced numerals designate corresponding parts throughout the different views.

DETAILED DESCRIPTION

Figure 1:
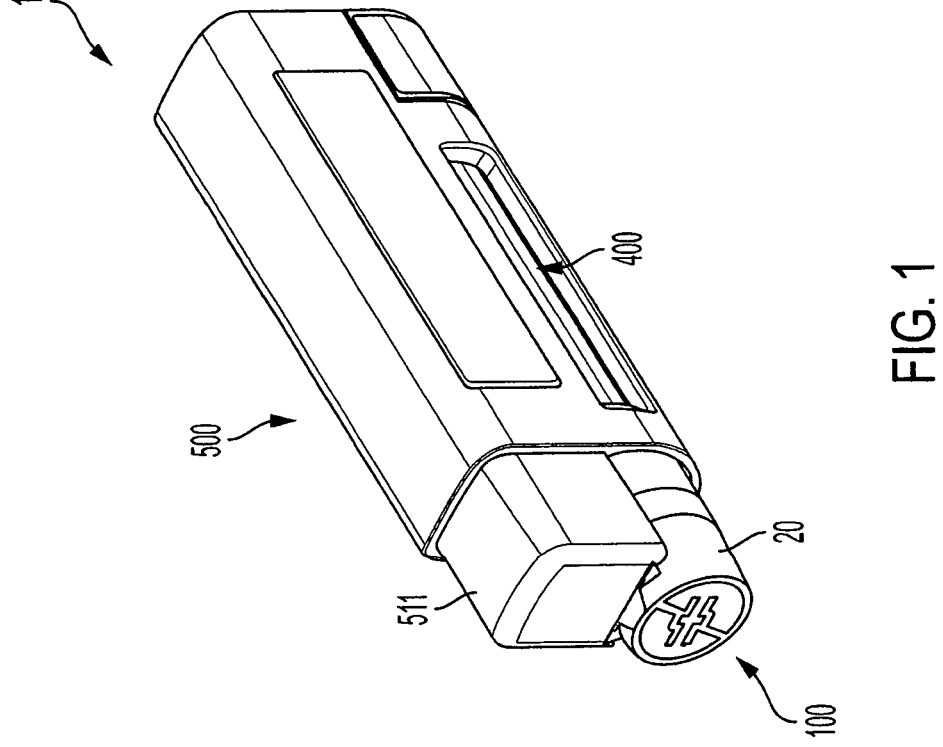
FIG. 1 is a perspective view of a drug delivery device according to one embodiment.

The present disclosure relates to drug delivery devices having needle assemblies that are removably attachable to another portion of the drug delivery device. This other portion of the drug delivery device will be referred to herein as a drug device, while the combination of the needle assembly with the drug device will be referred to herein as a drug delivery device. A drug device may, in some embodiments, include the portion of the drug delivery device that contains or is configured to contain a medicament.

In one aspect, a needle assembly is configured to be attached to a drug device by a user without requiring the user to contact and/or view the needle of the needle assembly.

In another aspect, a needle assembly is configured to be removed from a drug device by a user without requiring the user to contact the needle of the needle assembly, and in some embodiments, without requiring the user to view the needle of the needle assembly.

As discussed above, in some embodiments, the drug device portion of the drug delivery device may contain a medicament. The term "medicament" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medicament as used in the device may be formulated with one or more excipients. The device is operated in a manner generally as described herein by a patient, caregiver or healthcare professional to deliver medicament to a person.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

Figure 2:
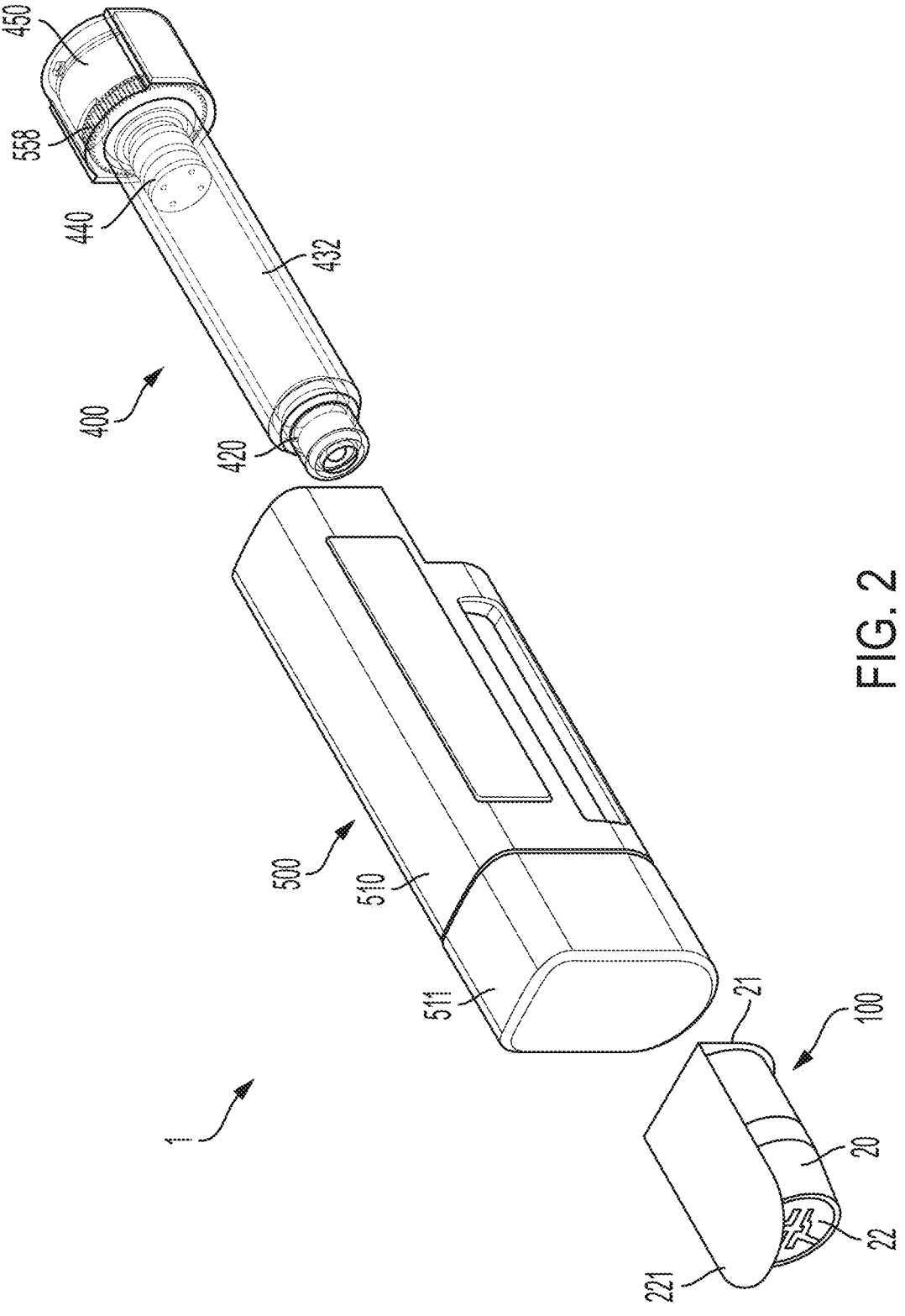
FIG. 2 is an exploded view of the drug delivery device of FIG. 1, where the drug delivery device is separated into a needle assembly, a drug device, and a medicament container.

An illustrative embodiment of a drug delivery device is shown in FIG. 1, with an exploded view of the drug delivery device shown in FIG. 2. The drug delivery device 1 may include a needle assembly 100, a drug device 500, and a medicament container 400. In some embodiments, the needle assembly and the medicament container are disposable components. The needle assembly may be configured to be used only once and replaced each time. In other embodiments, however, all of or portions of the needle assembly may be re-used. In some embodiments, the medicament container may be used to deliver medicament multiple times, as in a multi-dose arrangement. In other embodiments, the medicament container is configured to deliver all of its contents in a single dose. In some embodiments, all or portions of the drug device may be durable component(s) that may be reused many times. In other embodiments, however, the drug device is a single-use disposable component.

In some embodiments, as shown in FIG. 2, the medicament container 400 is formed as a generally cylindrical body having a septum 420 at a distal end thereof, an interior volume 432 to hold the medicament prior to dispensing, and a piston 440 disposed in the interior volume at a proximal end of the container 400 and moves distally through the interior volume 432 toward the septum 420 to expel medicament out of the medicament container. In some embodiments, a portion of a container drive for moving the piston may be part of the medicament container 400. In one embodiment, the piston 440 is driven by a container drive. In the embodiment of FIG. 2, such a container drive includes a first portion 450 located at a proximal end of the medicament container and, as will be discussed in more detail below, this first portion 450 of the container drive may cooperate with a second portion of the container drive, which may be located on the drug device.

Figure 3:
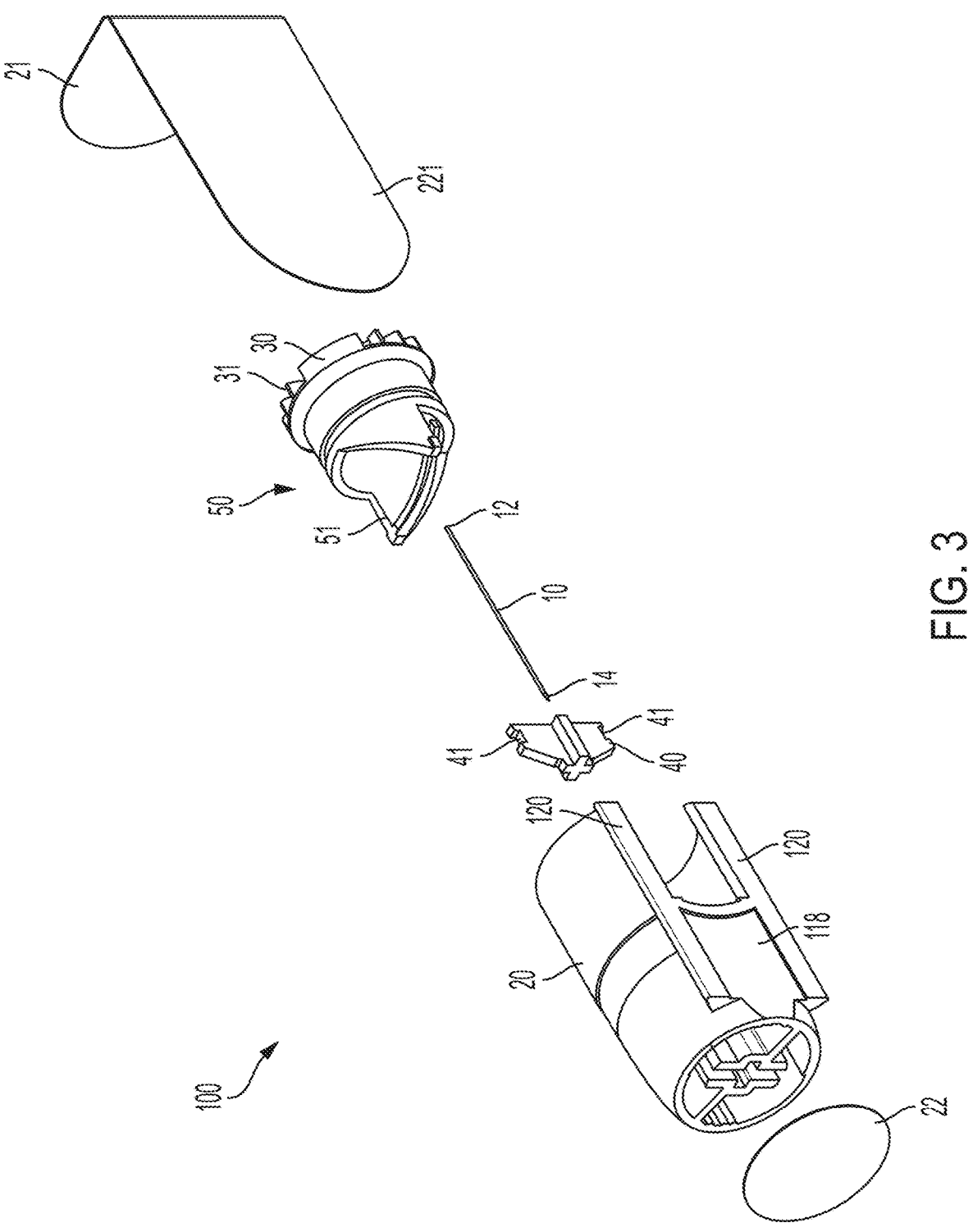
FIG. 3 is an exploded view of the needle assembly of FIG. 2.

An exploded view of the needle assembly is shown in FIG. 3. In this illustrative embodiment, the needle assembly 100 includes a generally cylindrical carrier 20 having a relatively flat section 118 formed with rails 120, a needle hub 40 (which may be wing-shaped as shown), a needle 10, a cam 50, a proximal cover 21 and a distal cover 22. The needle 10 includes a proximal end 12 and a distal end 14. In some embodiments, the needle 10 may be fixed to the needle hub 40 such that movement of the hub 40 causes the needle 10 to move as well.

In the illustrative embodiment of FIG. 3, the cam 50 includes drive helices 51 that engages within a notch 41 disposed on the hub 40 to move the needle hub 40 in deployment and/or retraction directions as the cam rotates relative to the carrier 20, as will be explained below. The cam 50 includes a driven gear 30 having teeth 31 that are driven by a drive element, such as a drive gear on the drug device. Other suitable drive elements may be employed as aspects disclosed herein are not so limited. For example, the drive element may be configured as a cam linkage, a rack gear, a worm gear, etc. Thus, deployment and retraction of the needle are driven by a needle drive mechanism on the drug device, as will be explained below.

In some embodiments, the proximal cover 21 is a peelable seal that may be removably affixed to the carrier 20, e.g. via a suitable adhesive. The proximal cover 21 may have a pull tab 221 that may be easily graspable to facilitate removal. In this regard, the distal position of the pull tab 221 may extend beyond the distal end of the needle assembly facilitating ease of grasping and manipulation. However, other types of covers may be used, such as a cap that engages with the carrier, e.g. via threads or other mechanical interlock, or an interference fit.

Figure 4A:
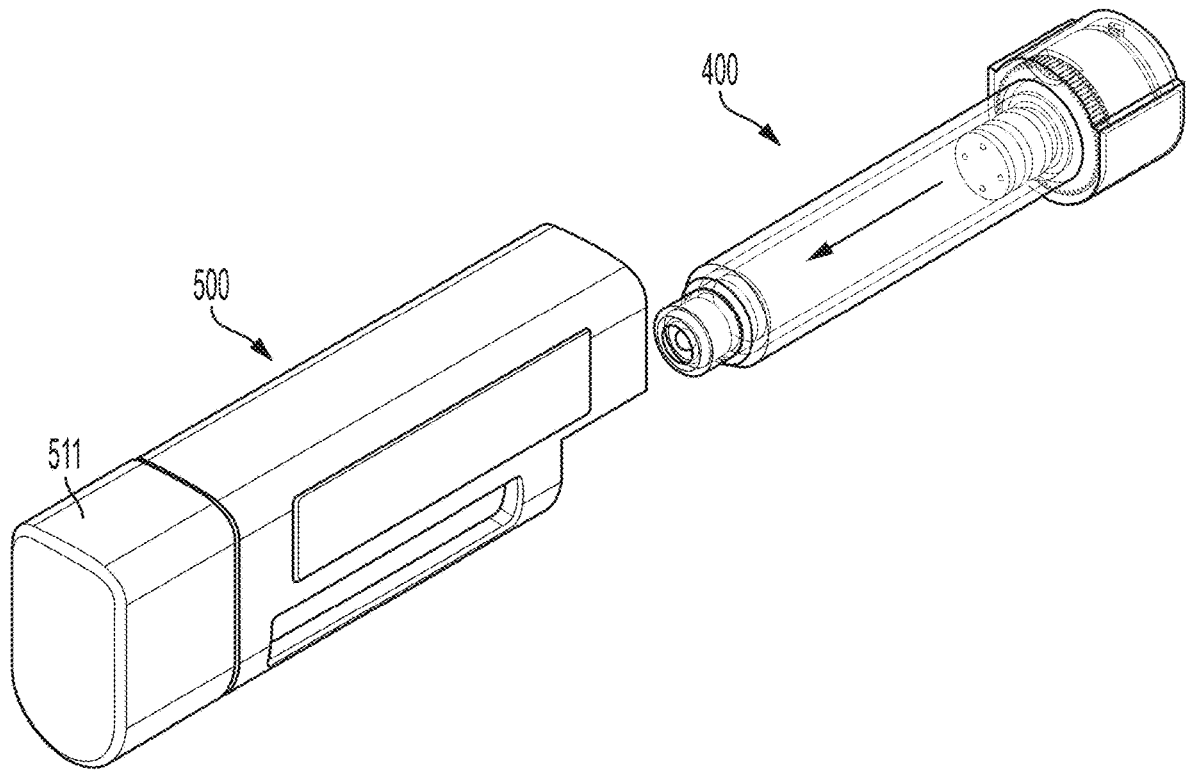
FIG. 4A depicts a perspective view of a medicament container being inserted into a drug device.
Figure 4B:
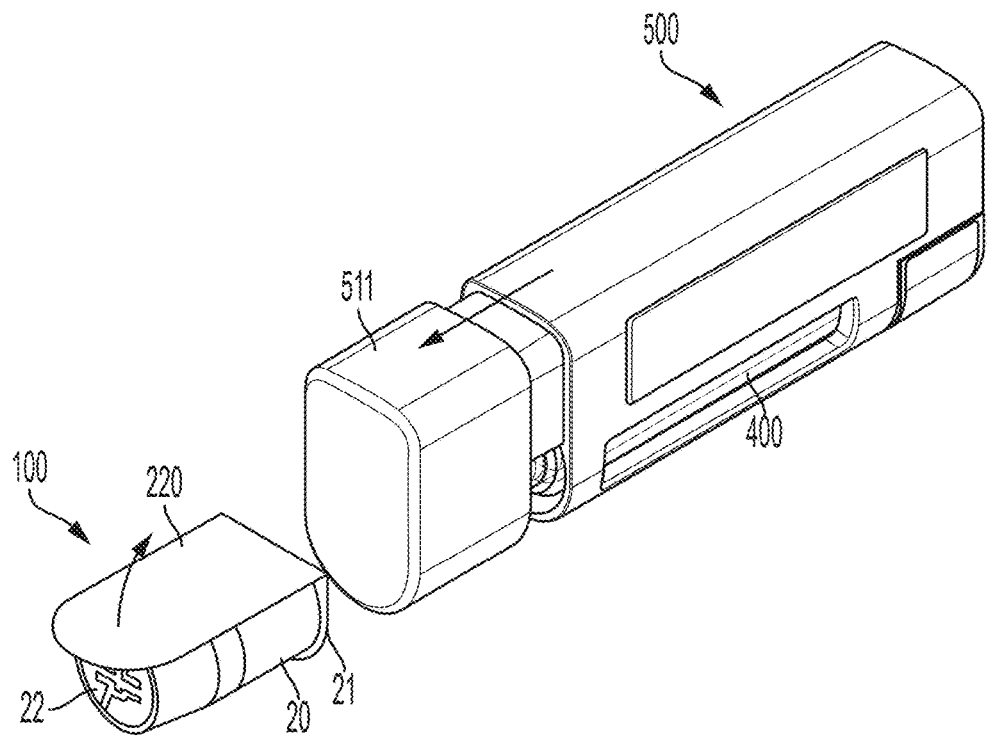
FIG. 4B depicts a needle assembly and drug device being prepared for coupling to one another.
Figure 4C:
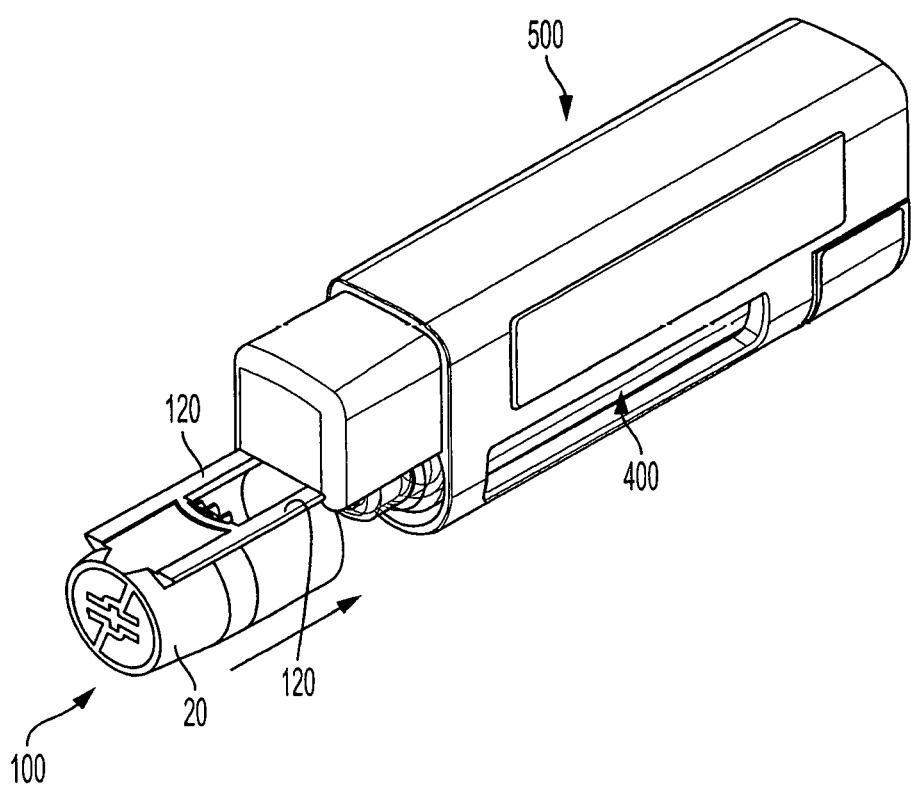
FIG. 4C depicts the needle assembly of FIG. 4B being coupled to the drug device.
Figure 4D:
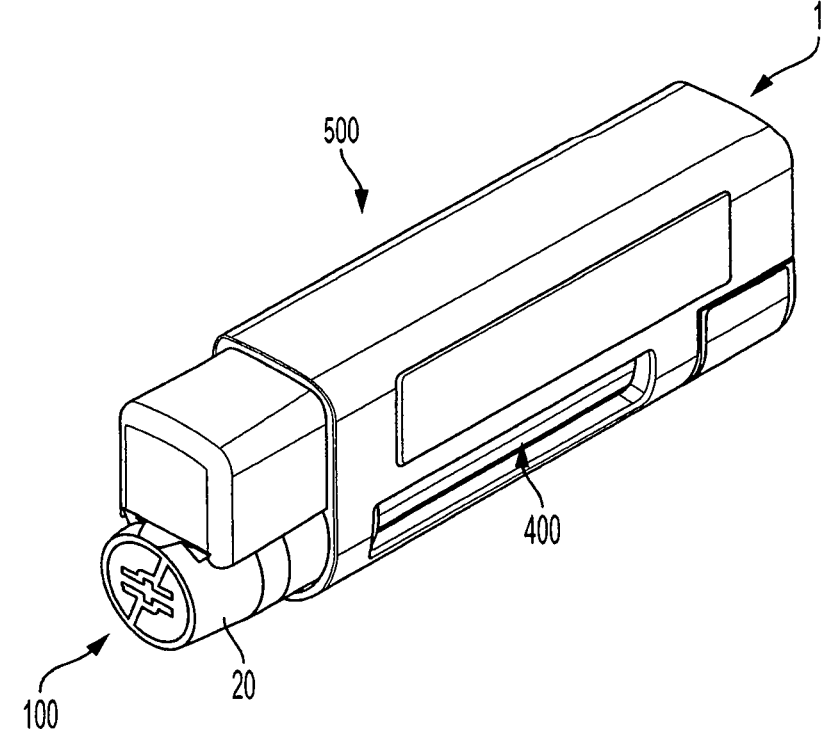
FIG. 4D depicts a fully assembled drug delivery device.

In some embodiments, the distal cover 22 is not configured to be removed, but instead is configured to be pierced through by a needle. In some embodiments, the distal cover may be a thin pierceable layer of material such as a foil seal, and may be affixed to the carrier via adhesive or other suitable arrangement. In other embodiments, however, the distal cover is configured to be removed. Examples of removable distal covers include, for example, a cap that engages with the carrier, e.g. via threads or other mechanical interlock, or an interference fit. Also, like the proximal cover, in one embodiment (not shown) the distal cover may include a peelable seal that includes a graspable portion extending beyond the edges of the needle assembly facilitating ease of grasping and manipulation A sequence of steps for assembly of the drug delivery device is shown in FIGS. 4A-4D. First, as seen in FIG. 4A, the medicament container is inserted distally with the septum end inserted into the drug device 500. Next, as seen in FIG. 4B, a cap 511, which fits over the distal end of the drug device, is removed. In addition, the proximal cover 21 is removed from the carrier 20 of the needle assembly 100 by peeling the pull tab 220 off of the carrier. The rest of the needle assembly 100 is housed inside the carrier 20. With the proximal cover 21 and the cap 511 removed, the carrier 20 can be coupled to the drug device 500 to couple the needle assembly to the drug device. As shown in FIG. 4C, the carrier 20 may include rails 120 that that slide into corresponding slots or grooves in the drug device 500 to couple the carrier to the drug device. The rails may fit in a dovetail like manner with the corresponding slots/grooves. FIG. 4D shows the drug delivery device 1 in its final assembled state. It should be appreciated that the order of the above is not important and that any suitable order for assembling the device may be employed.

Figures 1, 5A, 5B, 5C:
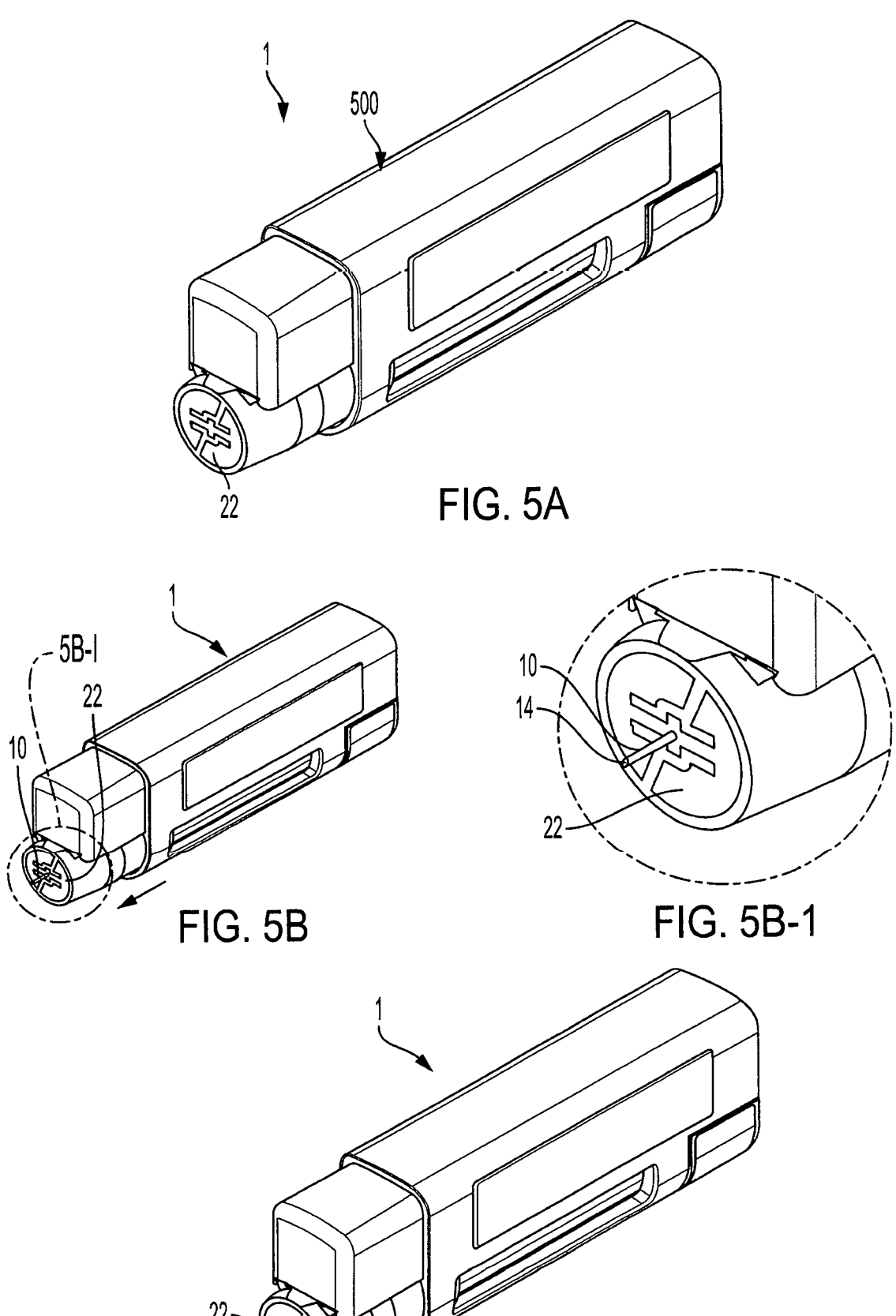
FIG. 5A depicts a perspective view of a drug delivery device that is ready to be used.
FIG. 5B depicts a needle of the drug delivery device of FIG. 5A moved to an extended position.
FIG. 5C depicts the needle of the drug delivery device moved to a retracted position.

A sequence of steps for operation of the drug delivery device is shown in FIGS. 5A-5E. FIG. 5A shows the drug delivery device 1 ready to be used. The drug delivery device is first placed against the subject's skin (not shown) such that the distal end of the device is in contact with the intended injection site. Next, the drug delivery device 1 is actuated to move the needle to an extended position, as shown in FIG. 5B. As seen in the enlarged view of FIG. 5B-I, when the needle moves to the extended position, the distal end 14 of the needle extends past the distal end of the carrier, which in this embodiment, is the distal cover 22. In this embodiment, the distal end 14 of the needle pierces through the distal cover 22 when moved to the extended position. With the needle in the extended position, the drug delivery device expels medicament from the medicament container, out through the needle, and into the subject. Next, after medicament delivery is complete, the drug delivery device 1 moves the needle from the extended position to a retracted position, as shown in FIG. 5C. In the retracted position, the distal end 14 of the needle may be located inside the carrier 20 to prevent inadvertent viewing and/or contact with the needle.

Figure 5D:
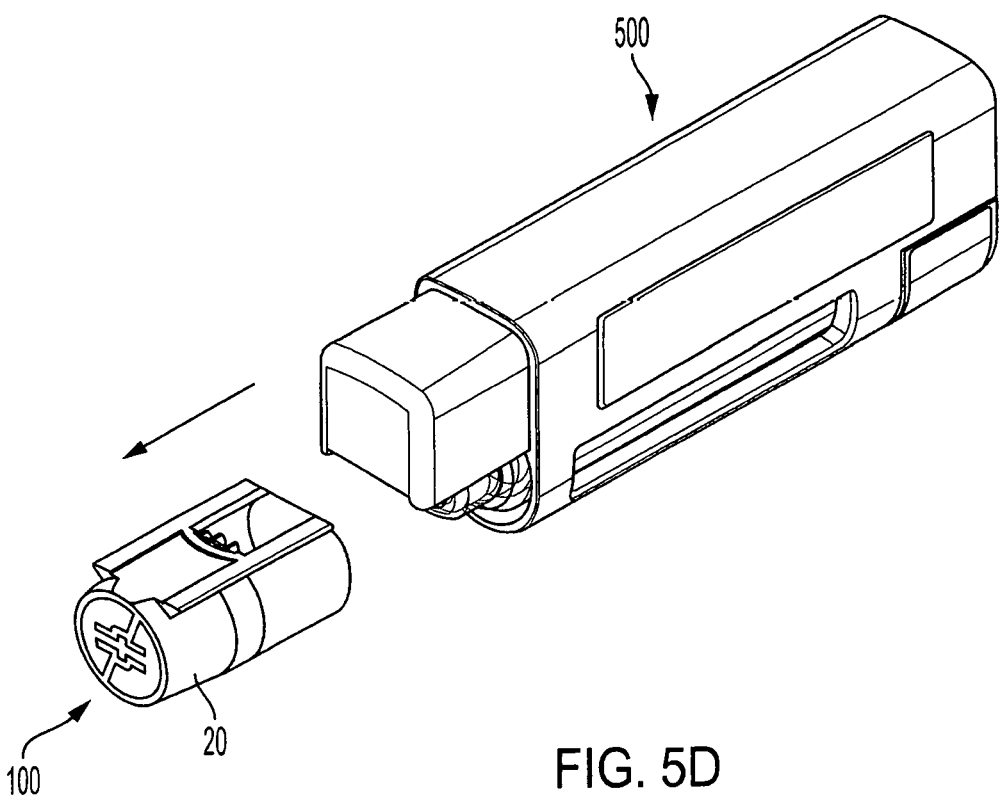
FIG. 5D depicts a needle assembly of the drug delivery device being removed.
Figure 5E:
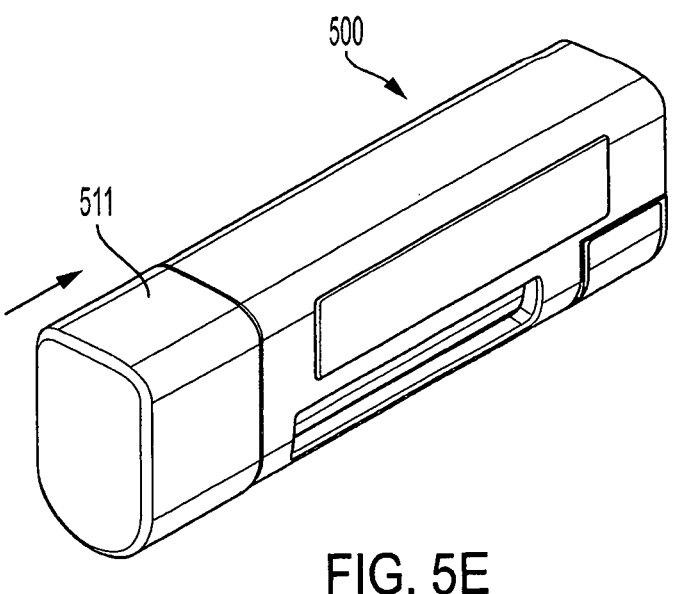
FIG. 5E depicts a cap being attached to the drug delivery device.

In some embodiments, the needle assembly is removed from the drug device after use, and may be discarded. FIG. 5D depicts the needle assembly 100 being removed from the drug device 500 by sliding the carrier 20 out of engagement with the drug device 500. Finally, as seen in FIG. 5E, a cap 511 may be placed on the distal end of the drug device, thereby covering distal end of the medicament container and the septum to close off the drug device.

Cross-sections of the drug delivery device as the drug delivery device undergoes a sequence of operational steps are shown in FIGS. 6A-6H.

Figures 6A, 6B:
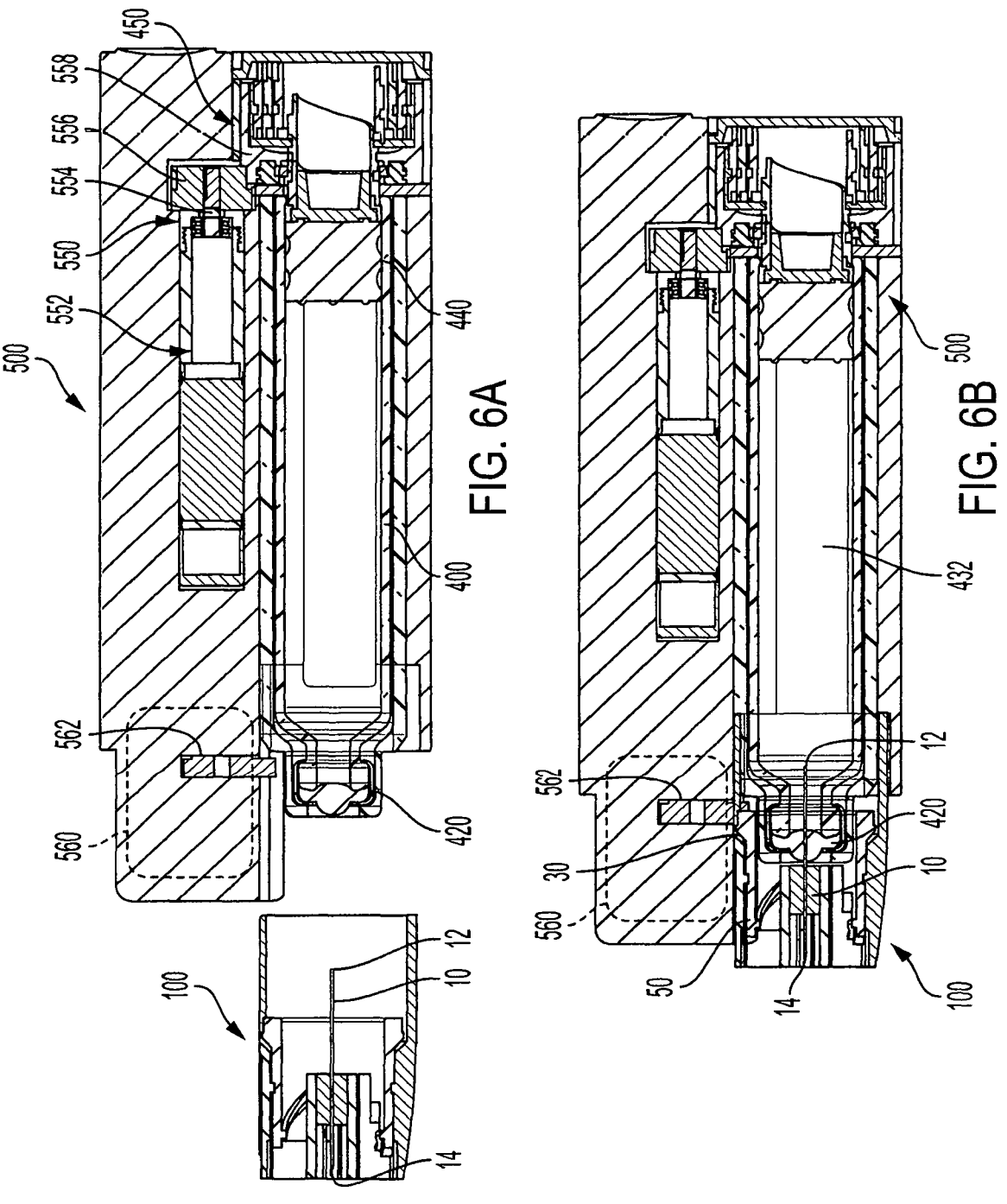
FIG. 6A depicts a cross-section of a drug delivery device with a needle assembly being initially separate from the drug device.
FIG. 6B depicts a cross-section of the drug delivery device of FIG. 6A with the needle assembly coupled to the drug device.

FIG. 6A shows the needle assembly 100 prior to coupling to the drug device 500. In FIG. 6A, the medicament container 400 has already been inserted into the drug device 500. The septum 420 has not yet been pierced by the needle of the needle assembly, and the piston 540 is in a proximal position, indicating that the medicament container has not yet expelled medicament. With the medicament container 400 coupled to the drug device, the first portion 450 of the container drive engages with a second portion 550 of the container drive located in the drug device to form a complete container drive. In the illustrative embodiment of FIG. 6A, the second portion 550 of the container drive includes a motor assembly 552 that turns a drive shaft 554 attached to a drive gear 556 that couples to the first portion 450 of the container drive, which in turn causes the piston 540 to move distally.

In one illustrative embodiment, the first portion 450 of the container drive includes a drive ribbon having a retracted configuration defining a spiral and an extended configuration defining a helix. The drive ribbon is movable from the retracted configuration to the extended configuration, where movement to the extended configuration advances the piston 440 in a distal direction. A drive member may be disposed radially inside the drive ribbon to engage and rotate the drive ribbon to move the drive ribbon between the retracted and extended configurations. Such a container drive including a drive ribbon is described in co-pending PCT Publication WO2019/112886, titled MEDICAL DELIVERY DEVICE WITH AXIALLY EXPANDABLE DRIVE RIBBON, published Jun. 13, 2019, which is hereby incorporated by reference in its entirety, and which is owned by the Applicant of this application.

Other container drive mechanisms may be used, as this aspect is not so limited.

In some embodiments, the motor assembly 552 drives a drive gear 556 that couples to a driven gear 558 (see also FIG. 2), which in turn is attached to a cam that converts rotational motion to translational motion of the piston 440. Other possible container drive mechanisms include, but are not limited to, a stepper motor, a pneumatic actuator, spring-driven mechanisms, whether linear or rotary, a syringe pump, or a servo motor as the disclosure is not so limited.

As also seen in FIG. 6A, the drug device includes a needle drive 560 that includes a drive gear 562. The drive gear may be driven by a motor or other suitable actuator. In some embodiments, the needle drive may share an actuator with the second portion 550 of the container drive, while in other embodiments, the needle drive may have its own actuator, such as a motor.

As seen in FIG. 6B, in which the needle assembly 100 has been coupled to the drug device 500, the drive gear 562 is configured to couple to a driven gear 30 of the needle assembly 100. In some embodiments, the driven gear 30 is coupled to or otherwise integrally formed with of a cam 50 of the needle assembly. Detailed views of the cam are shown in FIGS. 12A-12F. As also seen in FIG. 6B, with the needle assembly 100 fully coupled to the drug device, the proximal end 12 of the needle has pierced through the septum 420 of the medicament container and entered the interior 432 of the medicament container.

Figures 6C, 6D:
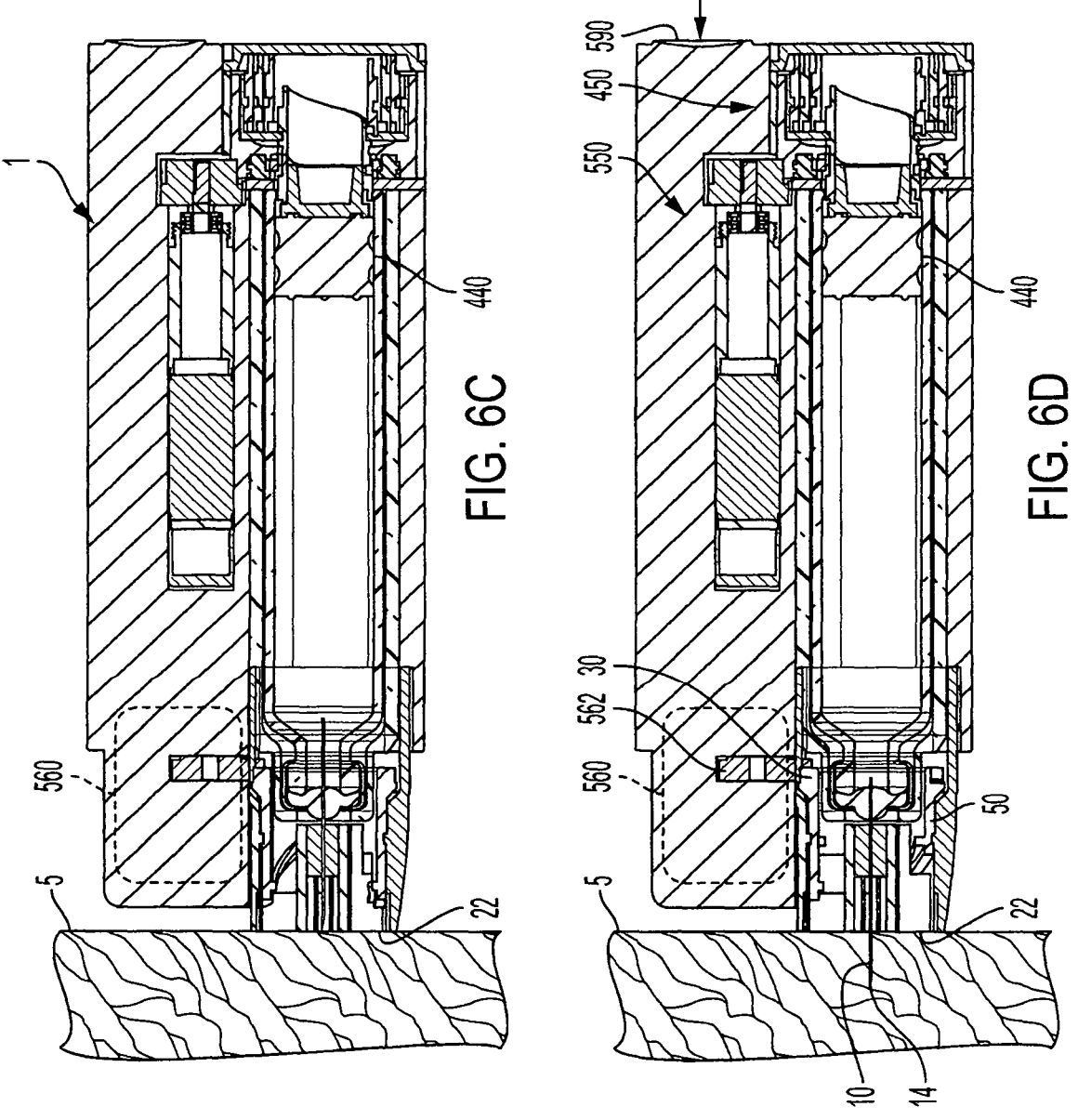
FIG. 6C depicts a cross-section of the drug delivery device where a distal end of the drug delivery device has been placed in contact with a subject's skin.
FIG. 6D depicts a cross-section of the drug delivery device with the needle in an extended position.

Turning to FIG. 6C, with the drug delivery device fully assembled, the drug delivery device 1 is brought into contact with the subject's skin 5 such that a distal end of the drug delivery device 1 is flush against the skin 5. In this illustrative embodiment, the distal cover 22 of the needle assembly is flush against the skin 5 and as such, the distal cover 22 need not be removed.

Figures 6E, 6F:
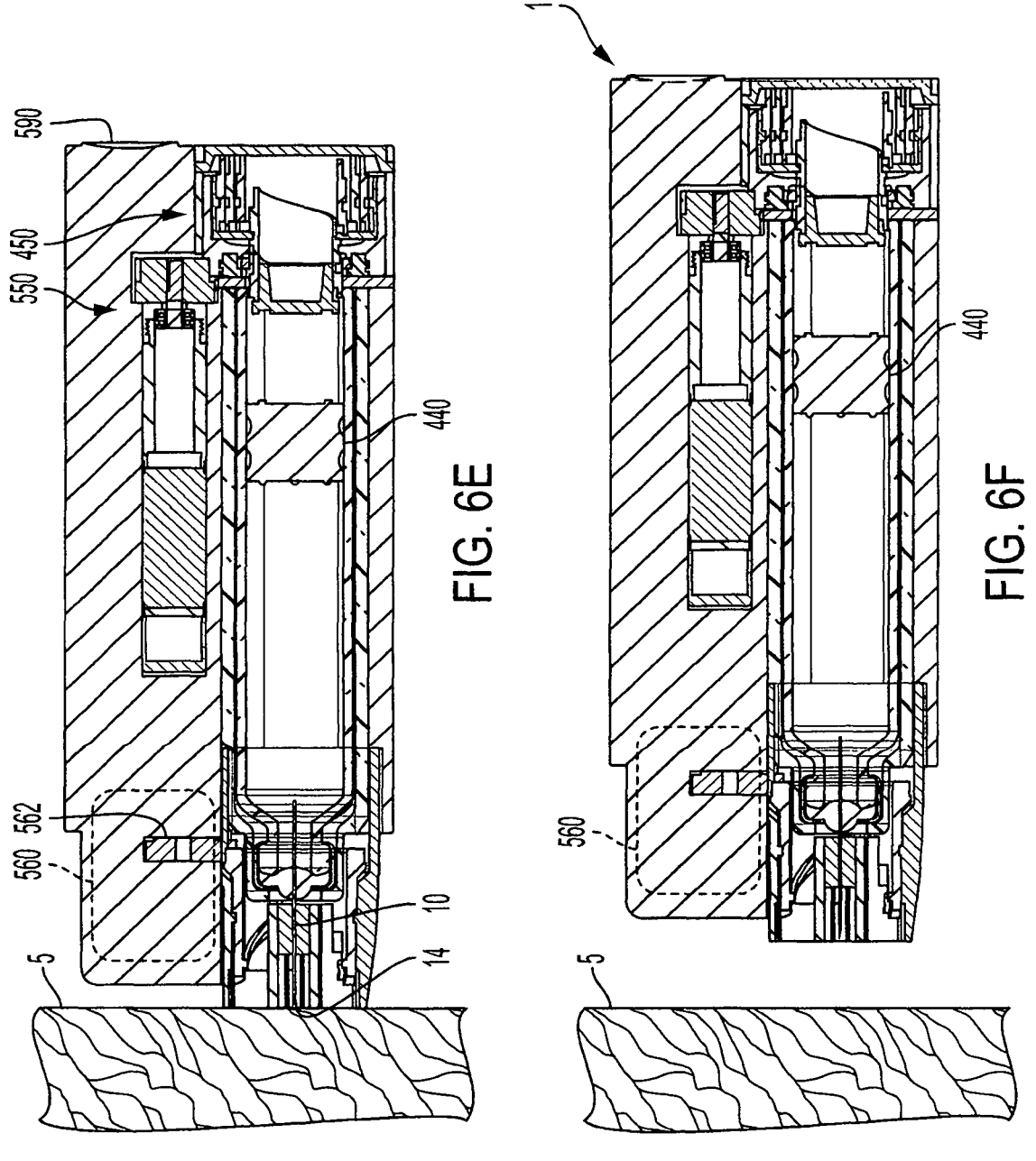
FIG. 6E depicts a cross-section of the drug delivery device with the needle in a retracted position.
FIG. 6F depicts a cross-section of the drug delivery device with the drug delivery device removed from the subject's skin.

The drug delivery device 1 is then actuated to extend the needle into the skin. As shown in FIG. 6D, actuation of the drug delivery device 1 occurs by pressing actuator button 590. In some embodiments, pressing the actuator button 590 may trigger a controller (not shown) to activate a motor (not shown) of the needle drive 560 to rotate drive gear 562 of the needle drive 560, which causes rotation of the driven gear 30, which in turn causes rotation of the cam 50. As will discussed in greater detail below, rotation of the cam 50 may cause distal movement of a needle hub 40 that is attached to a needle, causing the needle to move distally to an extended position. As a result, as shown in FIG. 6D, the needle is moved to an extended position in which the distal end 14 of the needle moves out of the carrier 20 and is pierced into the subject's skin 5. With the needle pierced into the subject's skin, the drug delivery device may proceed to expel medicament out of the medicament container and through the needle. In this regard, the second portion 550 of the container drive is activated to drive the first portion 450 of the container drive, causing the piston 440 to advance distally. As seen in FIG. 6E, the piston 440 has moved distally to expel medicament out through the needle and into the subject's skin.

Following delivery of medicament to the subject, the needle 10 is retracted. As shown in FIG. 6E, retraction of the needle occurs with a motor or other actuator of the needle drive 560 being activated to rotate drive gear 562, which causes rotation of the driven gear 30, which in turn causes rotation of the cam 50. In some embodiments, the rotation directions of the drive gear, driven gear, and/or cam during needle retraction is opposite to the rotation directions of these same components during needle extension. Rotation of the cam 50 causes proximal movement of the needle hub 40, causing the needle 10 to move proximally to a retracted position. As a result, as shown in FIG. 6E, the needle is moved to a retracted position in which the distal end 14 of the needle is moved back into the carrier 20.

The drug delivery device is then removed from the subject's skin 5, as shown in FIG. 6F. In some embodiments, with the needle 10 in the retracted position inside the carrier, the needle cannot be seen by the subject.

It should be appreciated that aspects described herein are not limited with respect to the needle drive and/or piston drive arrangements as other suitable drive assemblies may be employed.

Figures 6G, 6H:
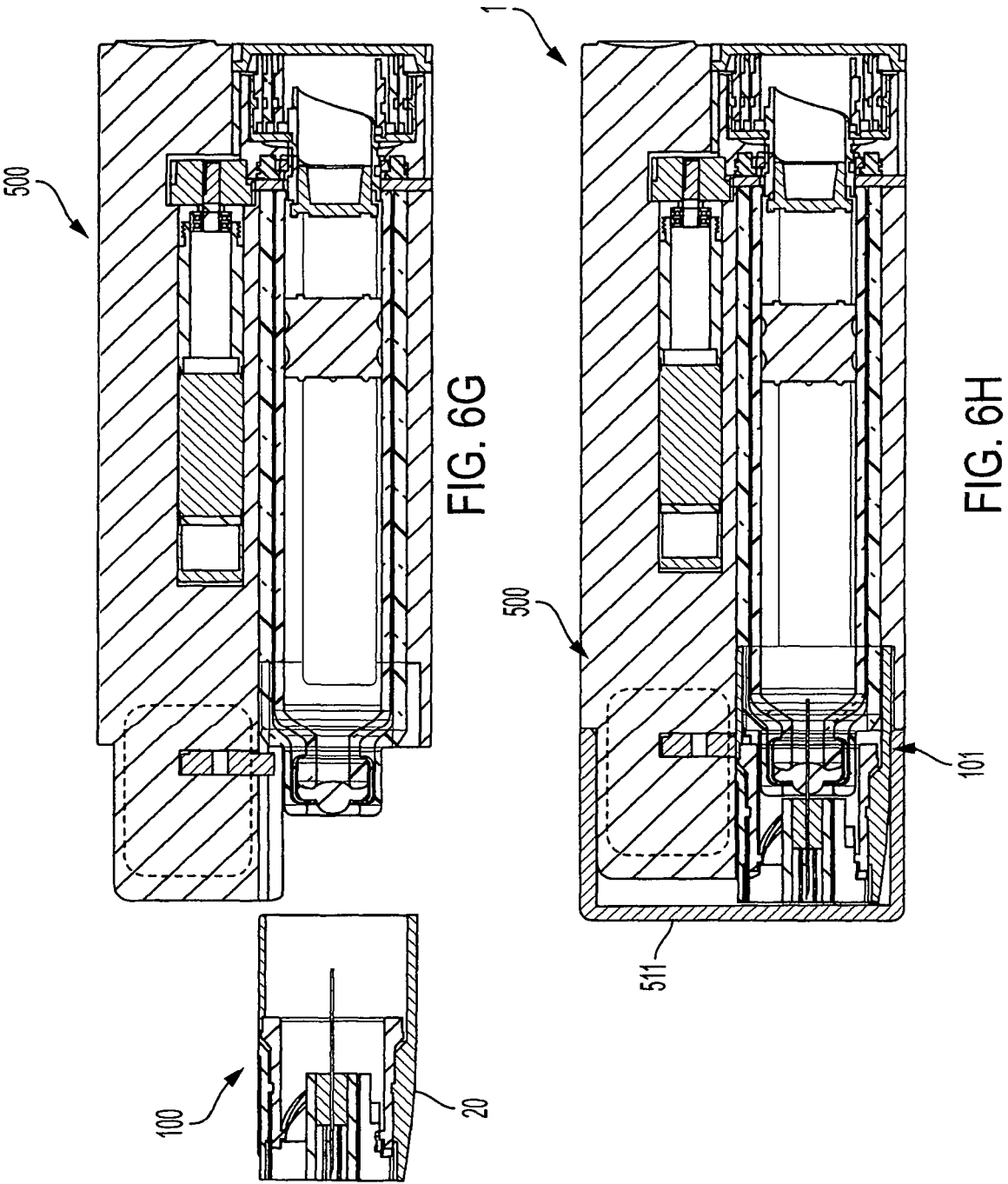
FIG. 6G depicts a cross-section of the drug delivery device with the needle assembly removed from the drug device.
FIG. 6H depicts a cross-section of the drug delivery device with a new needle assembly coupled to the drug device, and a cap covering the needle assembly.

After use, the needle assembly 100 may be removed from the drug device 500 and discarded, as shown in FIG. 6G. As shown in FIG. 6H, a new needle assembly 101 may be attached to the drug device, and the drug delivery device may be closed off by a cap 511. Alternatively, the cap may be installed without also installing a new needle assembly.

Figure 7:
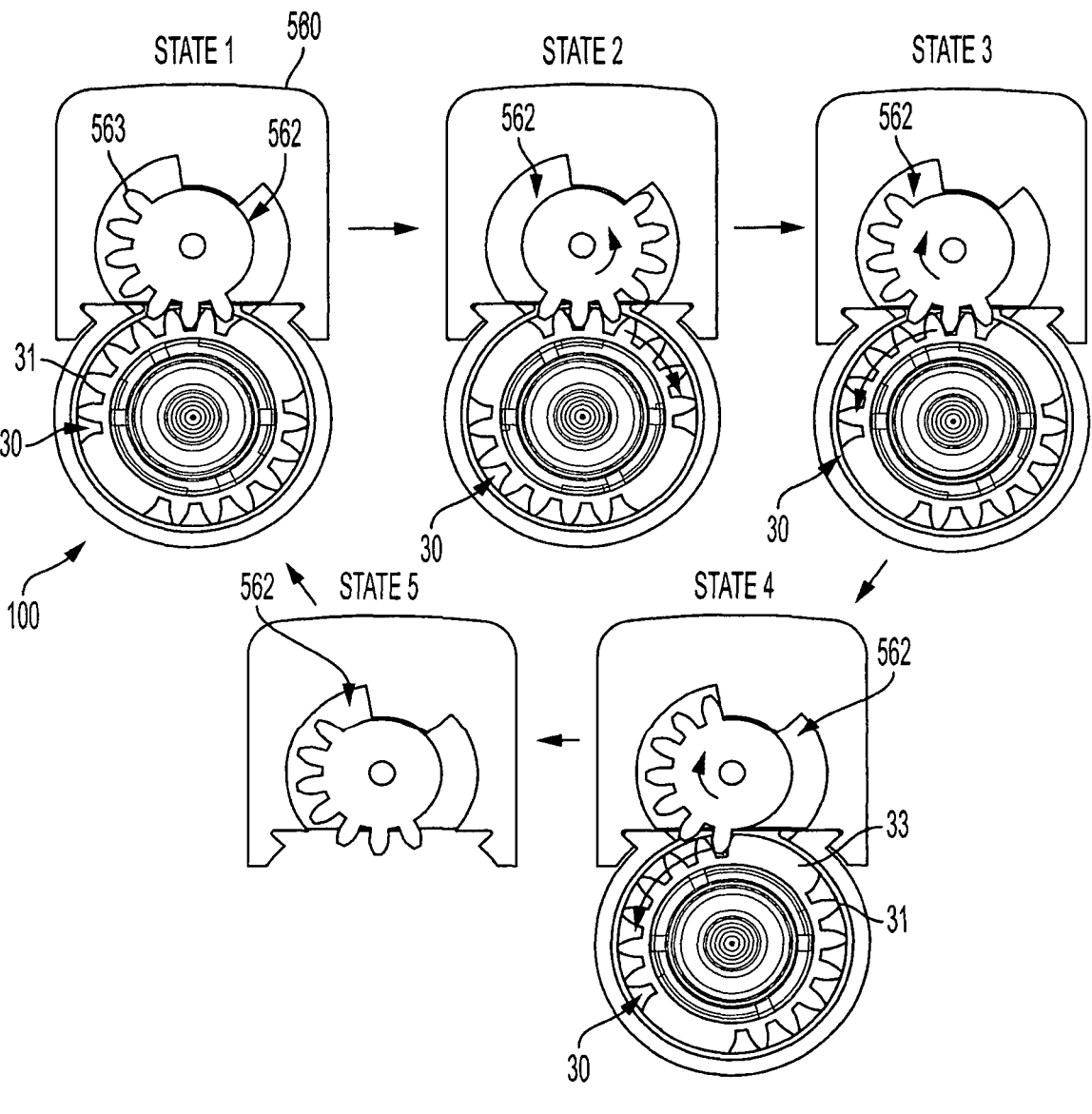
FIG. 7 depicts the interaction between a drive gear of the drug device and a driven gear of the needle assembly as a drug delivery device undergoes a sequence of operations.

FIG. 7 depicts the sequence of interactions between the drive gear of the drug device and the driven gear of the needle assembly as the drug delivery device undergoes a sequence of operations.

According to one aspect, the needle assemblies are assembled such that its components are in a ready position in which the assembly can be installed to a drug device. In some embodiments, the drive gear and the driven gear may each have a ready position that complement one another to permit the gears to be coupled to one another.

In State 1 of FIG. 7, the driven gear 30 of the needle assembly 100 is in its ready position, and the drive gear 562 of the drug device is in its ready position. With both gears in the ready position, the relative alignment of the teeth 363 of the drive gear 562 and the teeth 31 of the driven gear 30 permit the gears to mesh with one another, which in turn allows the needle assembly 100 to be coupled to the drug device 500.

In some embodiments, the drug device controls the drive gear 562 to turn to a pre-set rotational position to set the drive gear in the ready position. Moving the drive gear to a ready position may occur automatically in response to detection of a condition of the drug device. For example, the drug device may detect removal of a used needle assembly and, in response, automatically turn the drive gear to the ready position. In some embodiments, a user may instruct the drug device to move the drive gear to the ready position. For example, the user may interact with a user interface of the drug device, e.g. pushing a "prepare for needle assembly attachment" button, or by simply powering on the device.

In State 2 of FIG. 7, the drive gear 562 is rotated, driving the driven gear 30 in the opposite direction. In this illustrative embodiment, the drive gear 562 is rotated counter clockwise, causing the driven gear 30 to rotate clockwise. In this illustrative embodiment, clockwise rotation of the driven gear 30 causes needle extension, as will be discussed in further detail below.

Next, in State 3 of FIG. 7, to retract the needle, the drive gear 562 is rotated in the opposite direction to the direction it moved in State 2. In this illustrative embodiment, the drive gear 562 is rotated clockwise, causing the driven gear 30 to rotate counter clockwise. In this illustrative embodiment, counter clockwise rotation of the driven gear 30 causes needle retraction, as will be discussed in further detail below.

As shown in State 4 of FIG. 7, the drive gear 562 rotates clockwise until the driven gear 30 reaches a locked position. The needle assembly 100 is then removed from the drug device such that the driven gear 30 is disengaged from the drive gear 562. Finally, in State 5 of FIG. 7, the drive gear, which is no longer in engagement with a driven gear, returns to its ready position. A new needle assembly and driven gear can then be engaged to the drive gear, returning the sequence back to State 1.

In some embodiments, moving the driven gear into a locked position in State 4 serves as a feature to prevent re-use of the needle assembly. In the locked position, the driven gear may be rotationally oriented in a manner that prevents engagement of the driven gear to the drive gear.

Figure 8:
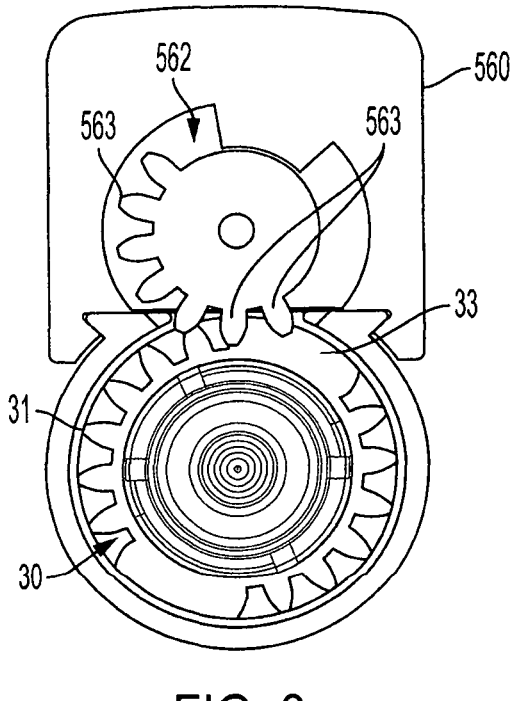
FIG. 8 depicts a used needle assembly being unable to re-attach to a drug device for re-use according to one embodiment.

In some embodiments, as shown in FIG. 8, the driven gear 30 may include a plurality of evenly spaced teeth 31, along with one or more areas that do not have the same teeth spacing, referred to as blocking portions 33. When the driven gear is in the locked position, the blocking portions 33 may be rotationally positioned to physically interfere with teeth 563 on the drive gear. As shown in FIG. 8, which depicts a used driven gear 30 in a locked position and the drive gear 562 in a ready position, one or more of the teeth 563 of the drive gear 562 may collide with the blocking portion 33 of the driven gear 30, preventing engagement between the gears. As a result, the needle assembly cannot be coupled to the drug device, thus preventing re-use of the drug assembly.

Figures 9A, 9B, 9C:
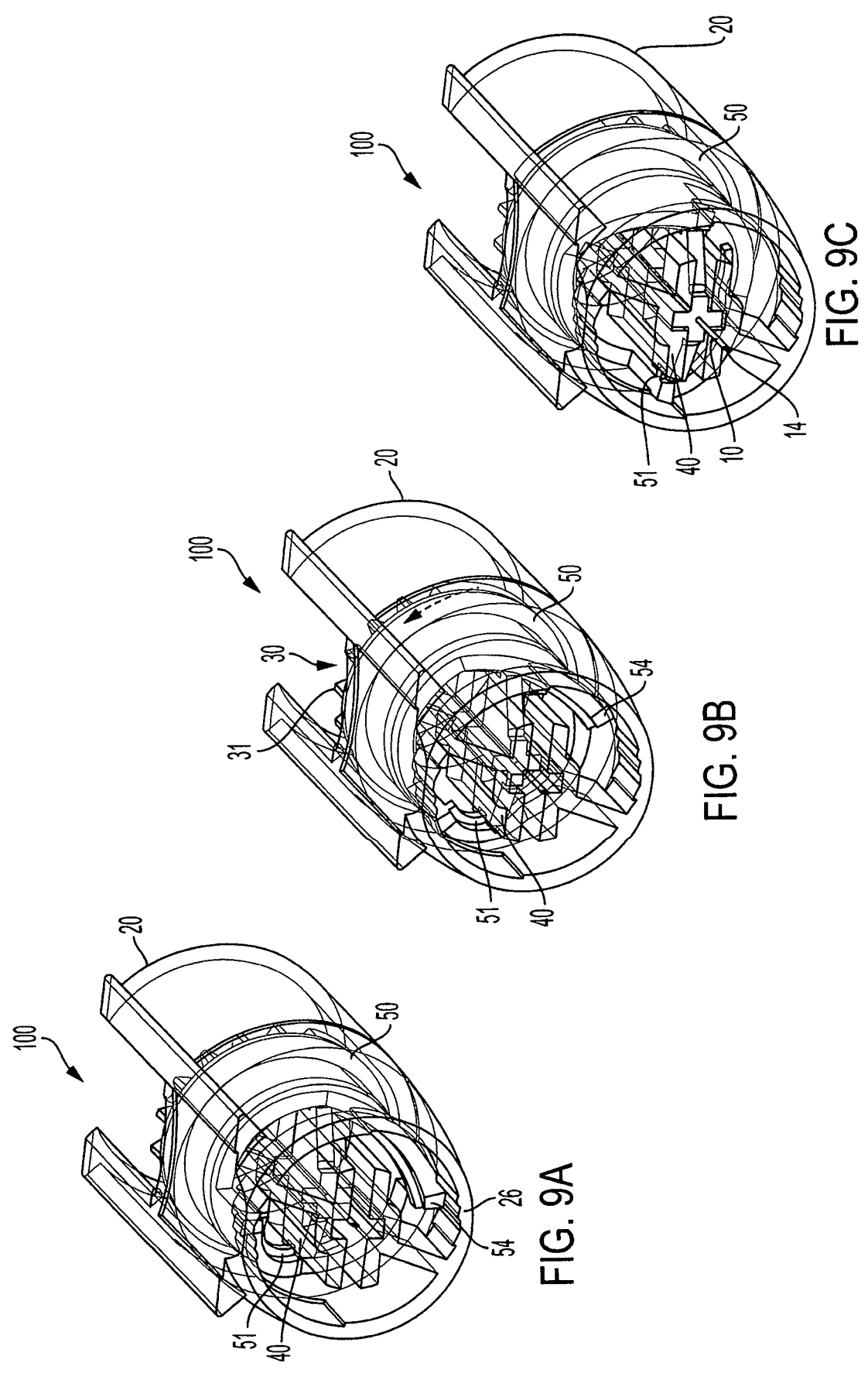
FIGS. 9A-9C depict the interaction between a cam, needle hub and carrier of a needle assembly as a drug delivery device undergoes a sequence of operations for needle extension.

FIGS. 9A-9C depict the interaction between the cam 50, needle hub 40 and carrier 20 of a needle assembly 100 as a drug delivery device undergoes a sequence of operations for needle extension. In FIG. 9A, the cam 50 is shown in the ready position. The cam includes a protrusion 54 that interacts with protrusions and indentations 26 on the carrier to form a detent, where rotation of the cam 50 is resisted by the protrusions and indentations 26 on the carrier until a sufficient amount of force is applied to the cam to rotate the cam protrusion 54 past the carrier protrusions 26. In some embodiments, the detent may function similar to a ratchet and pawl arrangement, where the protrusion 54 on the cam functions as a pawl and the protrusions and indentations 26 on the carrier function as a ratchet.

The needle hub 40 is mounted to drive helices 51 on the cam. In this regard, the notches 41 formed in the wing tips of the needle hub (see also FIGS. 3 and 13A-13D). Thus, rotation of the cam in a first direction moves the hub in an extension direction, and rotation of the cam in a second direction opposite to the first direction moves the hub in a retraction direction. This is illustrated in FIGS. 9B and 9C.

In FIG. 9B, the cam 50 is being turned in a counter clockwise direction due to turning of the driven gear 30 by the drive gear of the drug device. Rotation of the drive helices 51 of the cam in the counter clockwise direction causes the helices 51 to push the needle hub 40 in a distal direction due to the engagement of the helices 51 within the notches 41. As a result, shown in FIG. 9C, the needle 10 that is coupled to the hub 40 is moved to an extended position. Detailed views of the carrier are shown in FIGS. 11A-11F, detailed views of the cam are shown in FIGS. 12A-12F, and detailed views of the needle hub are shown in FIGS. 13A-13D for ease of reference of the relevant components and structures.

Figures 10A, 10B, 10C:
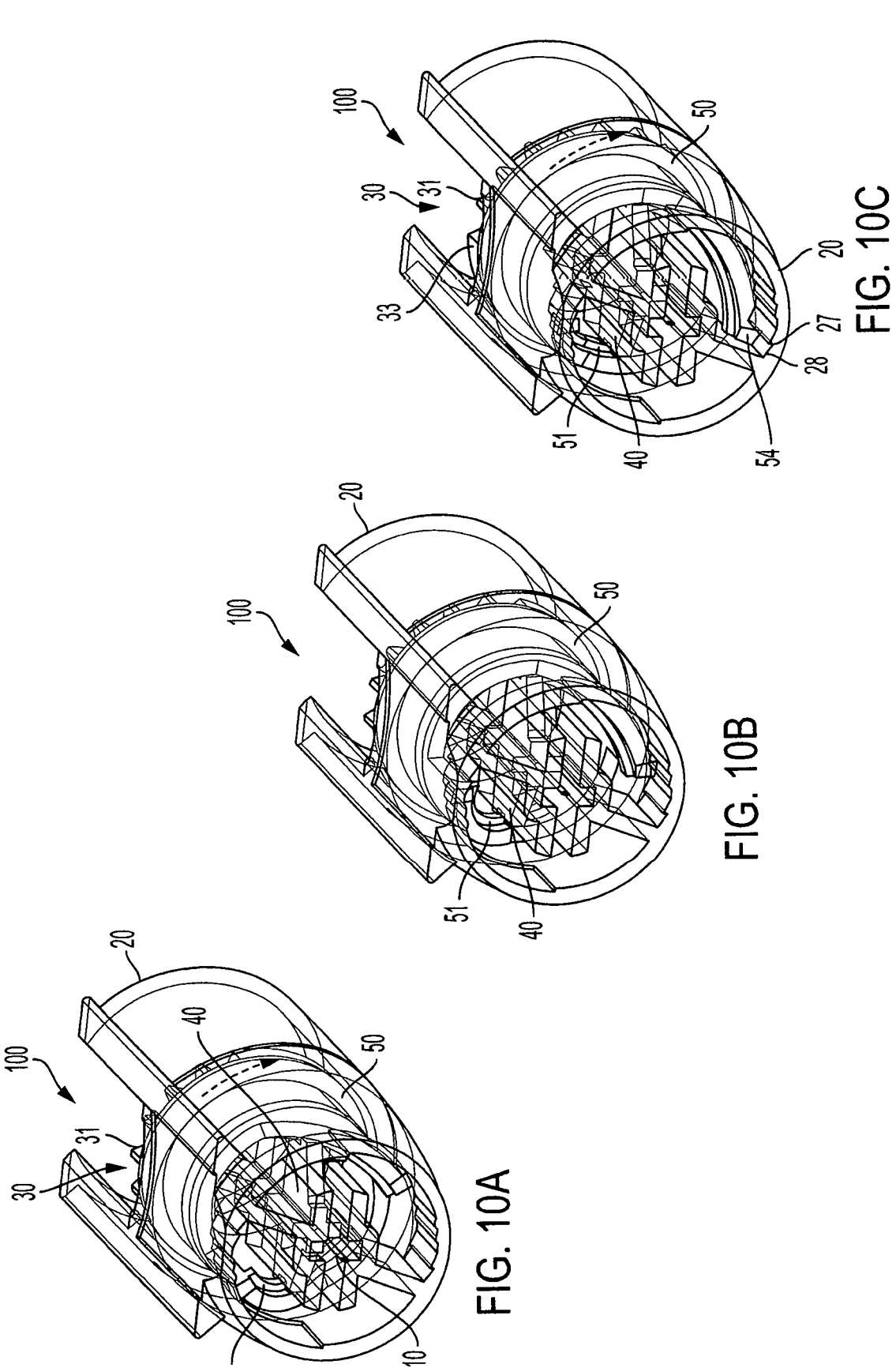
FIGS. 10A-10C depict the interaction between a cam, needle hub and carrier of a needle assembly as a drug delivery device undergoes a sequence of operations for needle retraction.

FIGS. 10A-10C depict the interaction between the cam, needle hub and carrier of the needle assembly as the drug delivery device undergoes a sequence of operations for needle retraction. In FIG. 10A, the cam 50 is being turned in a clockwise direction due to turning of the driven gear 30 by the drive gear of the drug device. Rotation of the drive helices 51 of the cam in the clockwise direction causes the helices 51 to pull the needle hub 40 in a proximal direction, again due to the engagement of the helices 51 within the notches 41. As a result, shown in FIG. 10B, the needle 10 that is coupled to the hub 40 is moved to a retracted position. In FIG. 10B, the cam is shown in a ready position in which the cam can be rotated to extend the needle.

In some embodiments, after medicament delivery, the cam is rotated to a locked position. In some embodiments, moving the cam to a locked position may prevent the needle assembly from being re-used. As shown in FIG. 10C, the cam is being rotated clockwise beyond the ready position of FIG. 10B. The protrusion 54 of the cam moves past a snap edge 27 of the carrier 20 and into a lock recess 28 of the carrier. When the protrusion 54 of the cam is received in the lock recess 28, the cam is locked in place and can no longer rotate in either direction relative to the carrier, thus preventing any further movement of the needle 10.

Figures 11A, 11B, 11C, 11D, 11E, 11F:
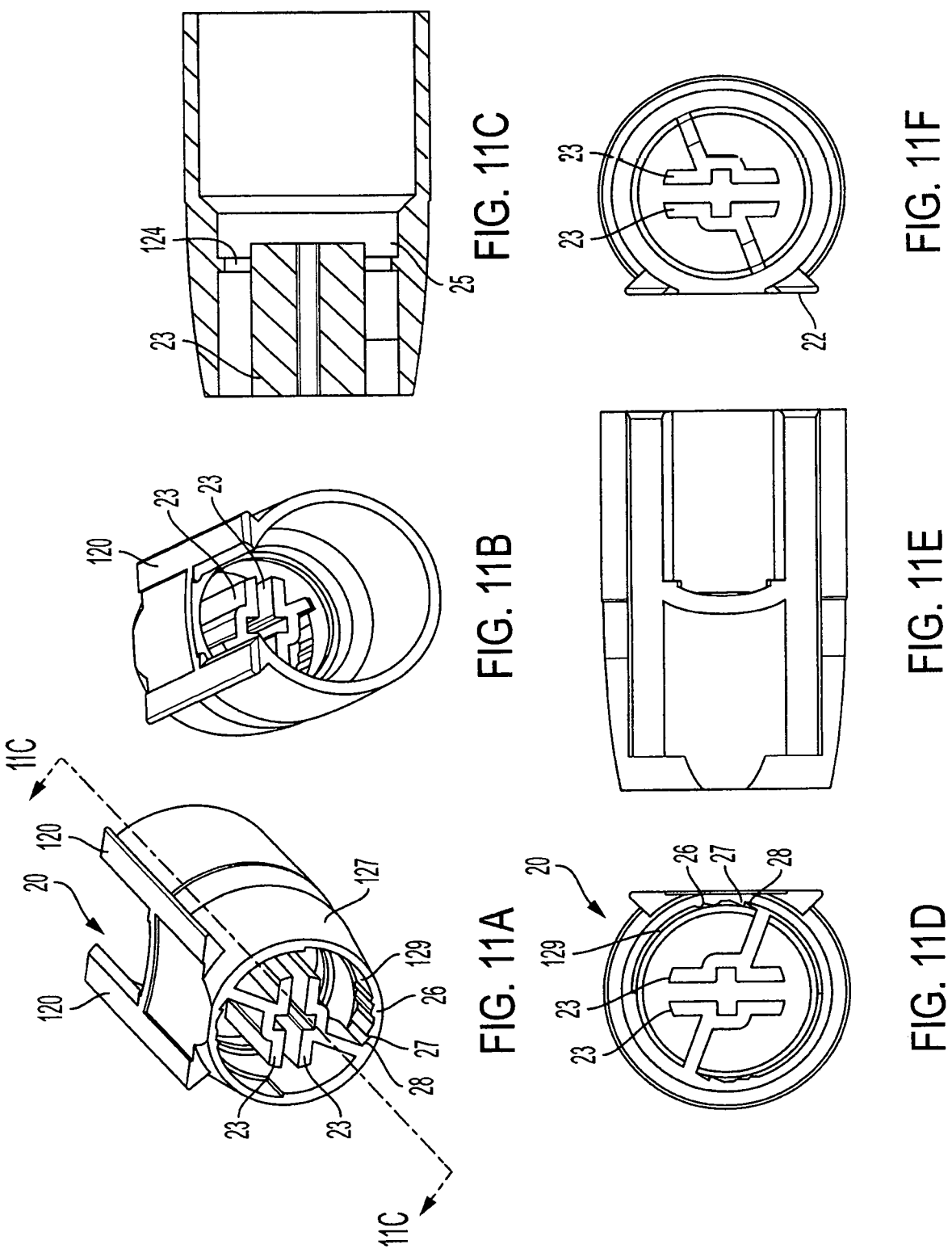
FIGS. 11A-11F depict views of a carrier of a needle assembly according to one embodiment.

FIGS. 11A-11F depict various views of the carrier 20 of the needle assembly according to one illustrative embodiment. As seen in FIGS. 11A and 11B and as discussed above, the carrier may include a cylindrical sidewall 127 including a dovetail features 120 that serve to couple the carrier to the drug device by sliding into corresponding slots in the drug device. As seen in FIGS. 11A, 11B, 11C (which is a cross section taken along line 11C-11C of FIGS. 11A), 11D and 11F, the carrier may include hub guides 23 that receive the needle hub. Hub guides 23 may be supported by radial support members that interconnect the hub guides to the carrier cylindrical sidewall 127. The guides 23 may be sized and shaped to prohibit rotation of the needle hub relative to the carrier and permit only linear sliding of the needle hub relative to the carrier. As seen in FIGS. 11A and 11D, the carrier may include surface features that interact with a protrusion on the cam to form a detent, as discussed above. The carrier may include protrusions and indentations 26 on an inner wall surface 129 of the carrier. The carrier may also include a snap edge 27 and a lock recess 28. Turning to the cross-sectional view of the carrier in FIG. 11C, the carrier may include a cam retention rib 124 that engages with a corresponding circumferential trough 524 on an outer surface of the cam 50 (see FIGS. 12A and 12E). The carrier may also have a cam rotational bearing surface 25 within which the cam rotates.

Figures 12A, 12B, 12C, 12D, 12E, 12F:
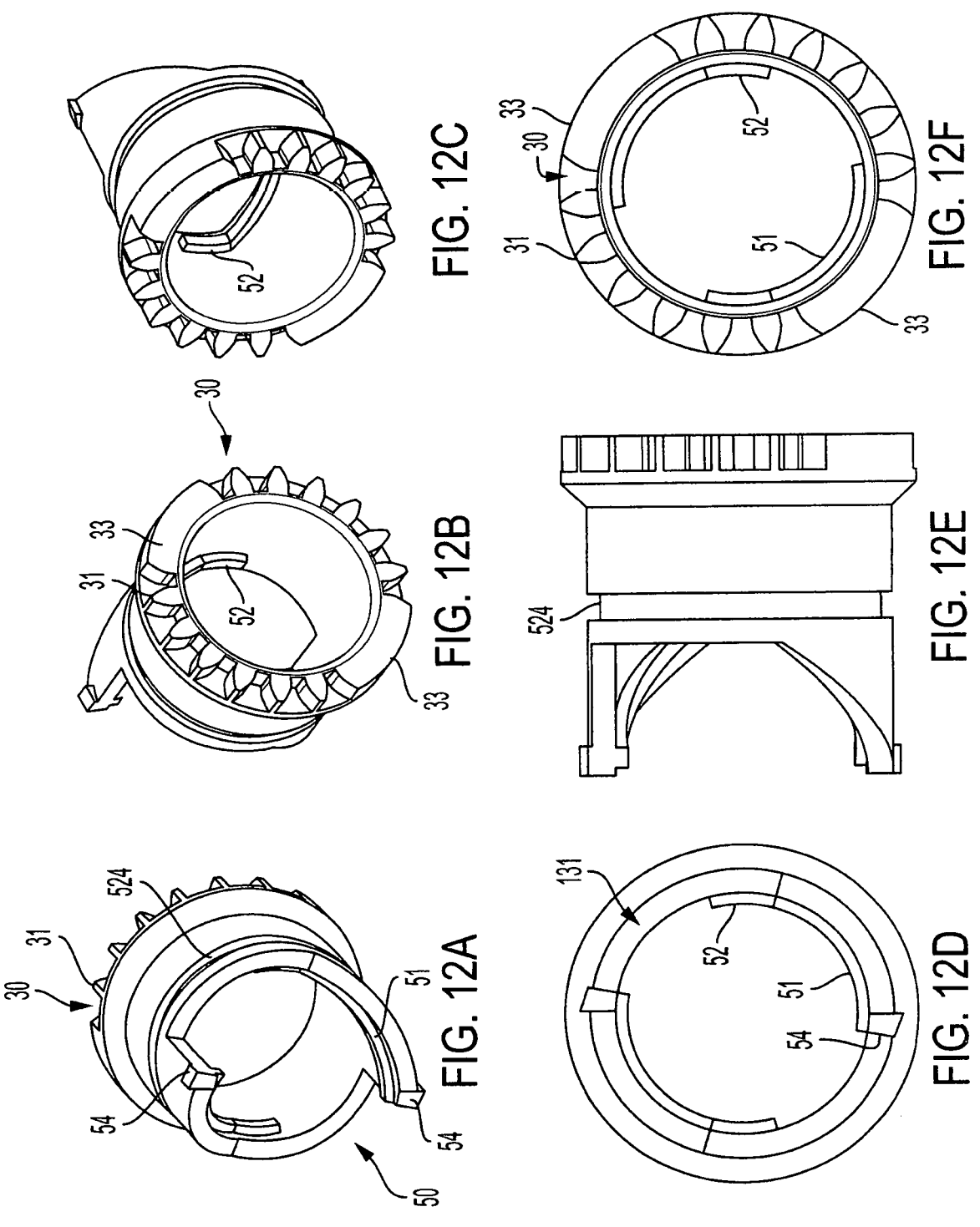
FIGS. 12A-12F depict views of a cam of a needle assembly according to one embodiment.

FIGS. 12A-12F depict various views of the cam 50 according to one illustrative embodiment. As seen in FIGS. 12A, 12B, 12C, and 12F, the cam may include a cylindrical body 131 with a driven gear 30 having a plurality of teeth 31 and a blocking portion 33 along one axial end of body 131. As seen in FIGS. 12A, 12D, and 12F, the cam may have hub drive helices 51 along the opposite axial end of body 131 that move the needle hub between extended and retracted positions. As also seen in FIG. 12A, the cam may include a protrusion 54 that interacts with surface features on the carrier to form a detent. As seen in FIGS. 12B, 12C, 12D and 12F, the cam may include a hub lock rib 52 that helps restrain movement of the needle hub during piercing of the medicament container septum by the needle and when the cam is in the locked position.

Figures 13A, 13B, 13C, 13D:
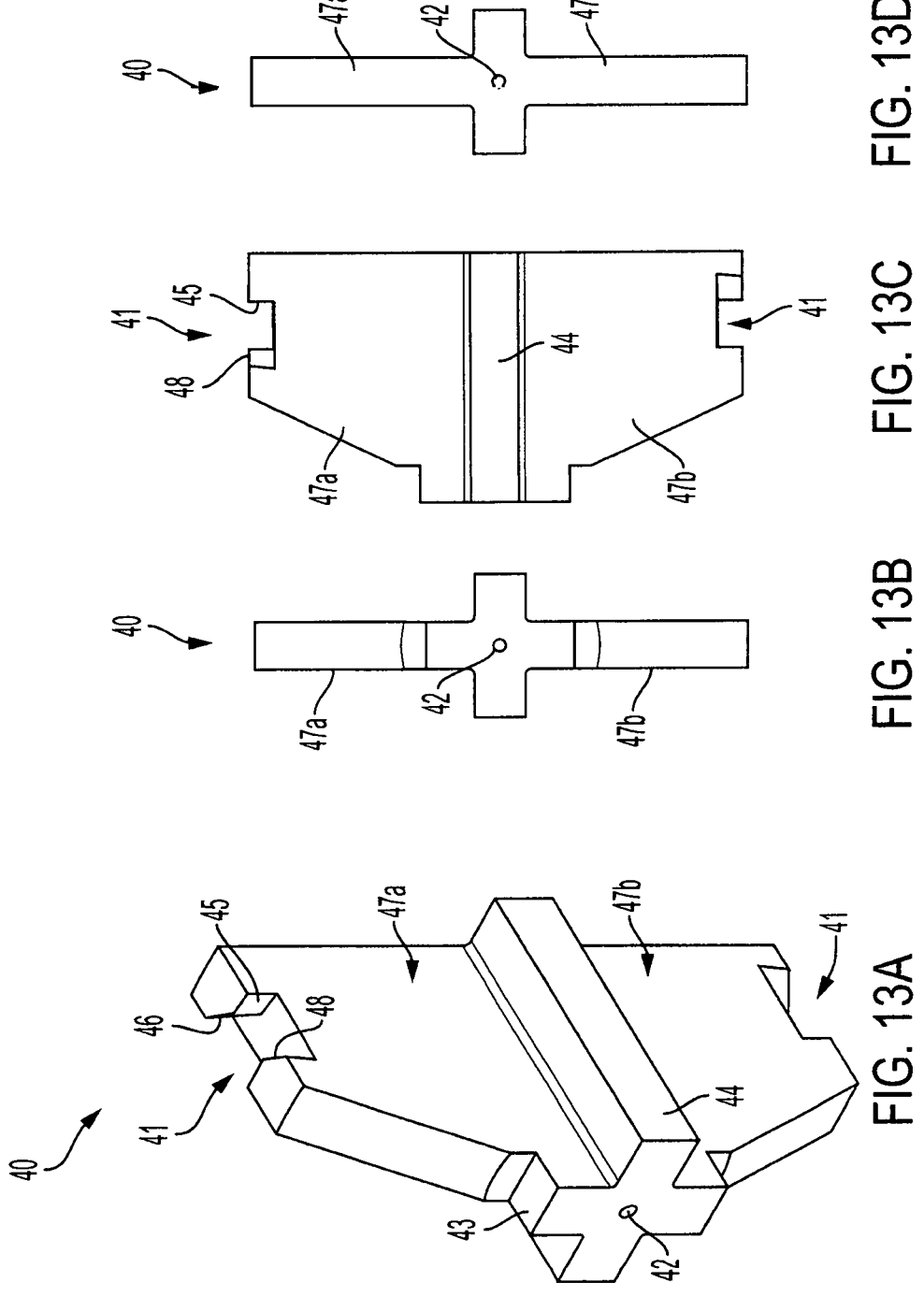
FIGS. 13A-13D depict views of a hub of a needle assembly according to one embodiment.

FIGS. 13A-13D depict various views of the needle hub 40 according to one illustrative embodiments. As seen in FIGS. 13A, 13B, and 13D, the hub may include a bore 42 for receiving a needle. The needle may be fixed to the hub in any suitable manner, for example via an adhesive, insert molding, mechanical interlock, welding, being integrally formed with the needle, UV light activated glue, or any other suitable arrangement.

As seen in FIG. 13A, the hub may include ribs 43, 44 that form a plus-sign shape and are sized to be received within the hub guide 23 of the carrier. As discussed above, the needle hub ribs 43, 44 complement the shape of the hub guide 23 of the carrier to permit the needle hub to slide linearly within the carrier but prohibit rotation of the needle hub relative to the carrier.

As also seen in FIG. 13A, the needle hub includes arms 47a and 47B, which may be wing-shaped, each with notch 41 formed in the outermost edge of the arm. The notches 41 have a plurality of contact surfaces that interact with different components of the needle assembly. The needle hub includes a first helical face 46 that is pushed distally by the hub drive helix of the cam to move the hub and the needle in an extension direction. The needle hub also includes a second helical face 48 that is pulled proximally by the hub drive helix of the cam to move the hub and the needle in a retraction direction. The needle hub may include a forward face 45. During septum piercing and when the cam is in the locked position, the hub lock rib 52 of the cam contacts against the forward face 45 of the needle hub to help restrain movement of the needle hub.

It should be understood that the drug devices shown are illustrative, as the needle assemblies described herein can be adapted for use with variously configured drug devices, including differently constructed pen-shaped medication injection devices, differently shaped injection devices, and infusion pump devices. The medication may be any of a type that may be delivered by such a drug device. The devices shown are intended to be illustrative and not limiting as the needle assemblies described may be used in other differently configured devices.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations. Furthermore, the advantages described above are not necessarily the only advantages, and it is not necessarily expected that all of the described advantages will be achieved with every embodiment.

Various aspects are described in this disclosure, which include, but are not limited to, the following aspects:

1. A drug delivery device, comprising: a needle assembly including a needle carrier, a needle hub moveable within the needle carrier, and a needle coupled to the needle hub; and a drug device having a needle drive, the needle carrier coupleable to the drug device to position a proximal end of the needle inserted through a septum in fluid communication within a container of the drug delivery device; and an actuator configured to activate the needle drive to move the needle hub distally from a retracted needle hub position to an extended needle hub position and to move the needle distally relative to the septum from a retracted needle position to an extended needle position.

2. The drug delivery device of aspect 1, wherein the needle drive includes a drive element.

3. The drug delivery device of aspect 2, wherein the needle assembly includes a driven gear that engages with the drive gear when the needle carrier is coupled to the drug device.

4. The drug delivery device of any one of aspects 1-3, wherein the needle drive includes a motor.

5. The drug delivery device of any one of aspects 1-4, further comprising a cam within the needle carrier, the cam being configured to drive the needle hub to move the needle in an extension direction and to drive the needle hub to move the needle in a retraction direction.

6. The drug delivery device of aspect 5, wherein the cam includes a driven gear and the needle drive includes a drive gear, wherein the driven gear engages with the drive gear when the needle carrier is coupled to the drug device.

7. The drug delivery device of any one of aspects 1-6, further comprising a medicament container, a container drive, and a piston that is moveable within the medicament container, wherein the container drive is configured to move the piston within the medicament container to expel medicament out of the medicament container and through the needle.

8. The needle assembly of any one of aspects 1-7, wherein the needle hub is disposed within the needle carrier and is coaxial relative to the needle carrier.

9. The needle assembly of any one of the preceding aspects, wherein the drug device includes a medicament container having a septum, wherein movement of the needle distally from the retracted needle position to the extended needle position comprises movement of the needle through and relative to the septum.

10. A method, comprising: providing a drug device having a drive gear;

providing a needle assembly including a needle carrier, a needle hub movable relative to the needle carrier, a needle coupled to the needle hub, and a cam configured to move the needle hub; mounting the needle assembly to the drug device to couple the cam to the drive gear; actuating the drive gear to rotate the cam to drive the needle hub distally to move the needle to an extended position; and actuating the drive gear to rotate the cam to drive the needle hub proximally to move the needle to a retracted position.

11. The method of aspect 10, further comprising a step of removing the needle assembly from the drug device.

12. The method of any one of aspects 10-11, wherein the drug device holds a medicament container; and further comprising a step of moving a piston relative to the medicament container to expel medicament from the medicament container and out through the needle.

13. The method of any one of aspects 10-12, wherein the step of coupling the needle carrier to the drug device comprises piercing a proximal end of the needle through a septum of a medicament container in the drug device.

14. The method of aspect 13, wherein movement of the needle from the retracted position to the extended position includes movement of the needle through and relative to the septum.

15. A needle assembly for coupling to a drug device and a container with a septum that includes a fluid, the needle assembly comprising: a needle carrier being coupleable to the drug device to pierce the septum, comprising a cam within the needle carrier, the cam having a driven gear; a needle hub coupled to the cam and movable relative to the needle carrier; and a needle coupled to the needle hub, wherein, in response to rotating the driven gear of the cam, the cam is configured to drive the needle hub to at least one of to move the needle in an extension direction and to drive the needle hub to move the needle in a retraction direction.

16. The needle assembly of aspect 15, wherein the cam and the driven gear are integrally formed.

17. The needle assembly of any one of aspects 15-16, wherein the needle hub includes notches engaged with respective helices formed on the cam.

18. The needle assembly of aspect 17, wherein the hub includes first and second arms, wherein the notches include a first notch formed at an outer edge of the first arm and a second notch formed at an outer edge of the second arm.

19. The needle assembly of aspect 18, wherein a first helical face is formed on the hub and is configured to be pushed distally by a helix of the cam to move the hub and the needle in an extension direction.

20. The needle assembly of aspect 19, wherein a second helical face formed on the hub that is configured to be pulled proximally by the helix of the cam to move the hub and the needle in a retraction direction.

21. The needle assembly of any one of aspects 15-20, wherein each notch includes a first helical face configured to be pushed distally by a helix of the cam to move the hub and the needle in an extension direction and a second helical face that is configured to be pulled proximally by the helix of the cam to move the hub and the needle in a retraction direction.

22. The needle assembly of any one of aspects 15-21, wherein the needle hub includes a forward face and wherein the cam includes a hub lock rib, wherein during septum piercing and when the cam is in a locked position, the hub lock rib of the cam contacts against the forward face of the needle hub to aid in restraining movement of the needle hub.

23. The needle assembly of any one of aspects 15-22, wherein the hub includes ribs that form a plus-sign shape and that are sized to be received within a hub guide formed in the carrier, wherein the needle hub ribs complement the shape of the hub guide of the carrier to permit the needle hub to slide linearly within the carrier and prohibit rotation of the needle hub relative to the carrier.

24. The needle assembly of any one of aspects 15-23, wherein the cam comprises a locked position configured to prevent the needle assembly from being re-used.

25. The needle assembly of aspect 24, wherein a the cam includes a protrusion and the carrier includes a snap edge and lock recess, wherein the protrusion of the cam is configured to move past the snap edge of the carrier and into the lock recess of the carrier, whereby when the protrusion is received in the lock recess, the cam is locked in place and is prevented from further rotation to prevent further movement of the needle.

26. The needle assembly of any one of aspects 15-25, wherein the carrier includes dovetail features configured to couple the carrier to the drug device by sliding into corresponding slots in the drug device.

27. The needle assembly of any one of aspects 15-26, wherein the driven gear of the cam includes a plurality of teeth and a blocking portion.

28. The needle assembly of aspect 24, wherein the driven gear of the cam includes a plurality of teeth and a blocking portion.

29. The needle assembly of aspect 28, wherein when the cam is in the locked position, the blocking portion is rotationally positioned so as to physically interfere with teeth on a drive gear of the drug device.

What is claimed is:

1. A drug delivery device, comprising:
a needle assembly including a needle carrier, a needle hub moveable within the needle carrier, and a needle coupled to the needle hub; and
a drug device having a needle drive comprising a motor, the needle carrier coupleable to the drug device to position a proximal end of the needle inserted through a septum in fluid communication within a container of the drug delivery device; and
an actuator configured to activate the needle drive to move the needle hub distally from a retracted needle hub position to an extended needle hub position and to move the needle distally relative to the septum from a retracted needle position to an extended needle position.

2. The drug delivery device of claim 1, wherein the needle drive includes a drive element.

3. The drug delivery device of claim 2, wherein the needle assembly includes a driven gear that engages with the drive gear when the needle carrier is coupled to the drug device.

4. The drug delivery device of claim 1, further comprising a cam within the needle carrier, the cam being configured to drive the needle hub to move the needle in an extension direction and to drive the needle hub to move the needle in a retraction direction.

5. The drug delivery device of claim 4, wherein the cam includes a driven gear and the needle drive includes a drive gear, wherein the driven gear engages with the drive gear when the needle carrier is coupled to the drug device.

6. The drug delivery device-needle assembly of claim 1, wherein the needle hub is disposed within the needle carrier and is coaxial relative to the needle carrier.

7. The drug delivery device of claim 1, wherein the drug device includes a medicament container having a septum and holding a medicament, wherein movement of the needle distally from the retracted needle position to the extended needle position comprises movement of the needle through and relative to the septum.

8. The drug delivery device of claim 1, further comprising a medicament container holding a medicament, a container drive, and a piston that is moveable within the medicament container, wherein the container drive is configured to move the piston within the medicament container to expel medicament out of the medicament container and through the needle.

9. A drug delivery device, comprising:
a needle assembly including a needle carrier, a needle hub moveable within the needle carrier, a needle coupled to the needle hub, a cam within the needle carrier, the cam having a driven gear and a drive surface engageable with the needle hub; and
a drug device having a needle drive, the needle carrier coupleable to the drug device to position a proximal end of the needle inserted through a septum in fluid communication within a container of the drug delivery device; and
an actuator configured to activate the needle drive to rotate the driven gear and the cam, in response to the rotation of the cam, the drive surface engages the needle hub such that the needle hub is moved distally from a retracted needle hub position to an extended needle hub position and the needle is moved distally relative to the septum from a retracted needle position to an extended needle position.

10. The drug delivery device of claim 9, wherein the cam and the driven gear are integrally formed.

11. The drug delivery device of claim 9, wherein the needle hub includes notches engaged with the drive surface of the cam.

12. The drug delivery device of claim 9, wherein the needle carrier includes a pair of hub guides configured to receive the needle hub and prohibit rotation of the needle hub relative to the needle carrier during axial movement.

13. The drug delivery device of claim 9, wherein the needle carrier includes dovetail features configured to slidably engage with corresponding slots in the drug device.

14. The drug delivery device of claim 9, wherein, in response to the rotation of the cam in a first direction, the needle is moved to the extended needle position.

15. The drug delivery device of claim 9, wherein, in response to the rotation of the cam in a second direction, opposite the first direction, the needle is moved toward the retracted needle position.

16. The drug delivery device of claim 9, wherein, in response to the rotation of the cam in the second direction, the driven gear is moved to a locked position.

17. A drug delivery device, comprising:

a needle assembly including a needle carrier, a needle hub moveable within the needle carrier, a needle coupled to the needle hub, a driven gear within the needle carrier; and a drug device having a needle drive gear, the needle assembly coupleable to the drug device to mesh the needle drive gear with the driven gear; and wherein, in response to the rotation of the drive gear, the driven gear is rotated in a first direction and the needle hub is moved from a retracted needle hub position to an extended needle hub position and the needle is moved relative to the needle carrier from a retracted needle position to an extended needle position.

18. The drug delivery device of claim 17, wherein the needle hub is configured to linearly move relative to the needle carrier during rotation of the driven gear.

19. The drug delivery device of claim 17, wherein the needle hub is configured to be prohibited from rotation relative to the needle carrier during movement relative to the needle carrier.

20. The drug delivery device of claim 17, wherein when the needle is in the needle extended position, a distal end of the needle is moved out of the needle carrier.

21. The drug delivery device of claim 20, wherein, in response to the rotation of the driven gear in a second direction, opposite the first direction, the needle is moved toward the retracted needle position and the distal end of the needle is moved back into the needle carrier.

22. The drug delivery device of claim 21, wherein, in response to the rotation of the driven gear in the second direction, a locked position is reached by the driven gear.

23. The drug delivery device of claim 22, wherein when the locked position is reached by the driven gear, a protrusion of the driven gear is received in a locked recess of the needle carrier.

24. The drug delivery device of claim 17, wherein the needle carrier includes dovetail features configured to slidably engage with corresponding slots in the drug device.

25. The drug delivery device of claim 17, wherein the driven gear includes a plurality of teeth and a blocking portion.

26. The drug delivery device of claim 25, wherein when the driven gear is in a locked position, the blocking portion is rotationally positioned so as to physically interfere with teeth on the needle drive gear.

27. The drug delivery device of claim 17, wherein the drug device includes a medicament container having a septum and holding a medicament.

* * * * *